United States Patent
Davies et al.

(10) Patent No.: US 10,280,429 B2
(45) Date of Patent: May 7, 2019

(54) PLANT PROMOTER FOR TRANSGENE EXPRESSION

(71) Applicant: Dow AgroSciences LLC, Indianapolis, IN (US)

(72) Inventors: John Davies, Indianapolis, IN (US); David Mann, Indianapolis, IN (US); James Patrick Connell, Indianapolis, IN (US); William T. Beeson, IV, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 86 days.

(21) Appl. No.: 15/298,467

(22) Filed: Oct. 20, 2016

(65) Prior Publication Data

US 2017/0114355 A1    Apr. 27, 2017

Related U.S. Application Data

(60) Provisional application No. 62/244,843, filed on Oct. 22, 2015.

(51) Int. Cl.
*C12N 15/82* (2006.01)

(52) U.S. Cl.
CPC ..... *C12N 15/8216* (2013.01); *C12N 15/8229* (2013.01); *C12N 15/8233* (2013.01); *C12N 15/8241* (2013.01)

(58) Field of Classification Search
None
See application file for complete search history.

(56) References Cited

U.S. PATENT DOCUMENTS 9,212,373 B2 * 12/2015 Rosichan ............ C12N 15/8216
2005/0050584 A1 * 3/2005 Gallie .................... C12N 9/88
800/278

FOREIGN PATENT DOCUMENTS

WO    WO 01/44457 A2 *  6/2001

OTHER PUBLICATIONS

Bolduc & Hake, Plant Cell 21:1647-58 (2009).*
GenBank Accession No. AY312169 (2003).*
Donald & Cashmore, EMBO J 9:1717-26 (1990).*
Kim et al., Plant Mol Biol 24:105-17 (1994).*
Dolferus et al., Plant Physiol 105:1075-87 (1994).*
Potenza et al., In Vitro Cell Dev Biol Plant 40:1-22, 2 (2004).*
Saha et al., In Silico Biol 7(1):7-19 (2007).*
Ashikari, M., et al. "Cytokinin oxidase regulates rice grain production." Science 309.5735 (2005): 741-745.
Bartrina, I., et al. "Cytokinin regulates the activity of reproductive meristems, flower organ size, ovule formation, and thus seed yield in *Arabidopsis thaliana*." The Plant Cell 23.1 (2011): 69-80.
Chuck, G., et al., "Floral meristem initiation and meristem cell fate are regulated by the maize AP2 genes ids1 and sid1." Development 135.18 (2008): 3013-3019.
Jackson, D., et al., "Expression of maize KNOTTED1 related homeobox genes in the shoot apical meristem predicts patterns of morphogenesis in the vegetative shoot." Development 120.2 (1994): 405-413.
Satoh-Nagasawa, N., et al. "A trehalose metabolic enzyme controls inflorescence architecture in maize." Nature 441.7090 (2006): 227-230.
Schmidt, R., et al. "Identification and molecular characterization of ZAG1, the maize homolog of the *Arabidopsis* floral homeotic gene AGAMOUS." The Plant Cell 5.7 (1993): 729-737.
Werner, T., and Schmulling, T. "Cytokinin action in plant development." Current opinion in plant biology 12.5 (2009): 527-538.

* cited by examiner

*Primary Examiner* — Russell T Boggs

(57) ABSTRACT

This disclosure concerns compositions and methods for promoting transcription of a nucleotide sequence in a plant or plant cell, employing a promoter from a *Zea mays* KN1 gene. Some embodiments relate to a promoter from a *Zea mays* KN1 gene that functions in plants to promote transcription of operably linked nucleotide sequences.

26 Claims, No Drawings

Specification includes a Sequence Listing.

SEQUENCE LISTING

<160> NUMBER OF SEQ ID NOS: 8

<210> SEQ ID NO 1
<211> LENGTH: 1407
<212> TYPE: DNA
<213> ORGANISM: Zea mays

<400> SEQUENCE: 1

```
ataaatttta acaagtaaaa agacttaact tggataaaaa aatgttttcg tggggcgggt      60
acatggggga acgtggacgg tcctcgtgaa actacgggga ttaaattttt ctccatttaa     120 atcccgcgg ggactaaatt agtctcatac ccatcccta ataggggaat tttccgcggg      180
gaattgggga tcgagtcccc attgtcatct ctactctgcg cacgtctgga tggtcgcgcc     240
tggggcccga acggttcacg atggcgcaga gggtcttatt tttcacagca gacctagatc     300
ttgcctctcg ggagggatcc cgtcggggag gagagatcct agggtgtgtc ttggtgtcag     360
caggccaccc aagacgcttc taatcgatgt agaaccgaag aaatgcgaag atttaaggta     420
gaggaaggct aaactagagc tactcctaat acaaaatgta aaaacgataa gtaaatttga     480
tctgatcgaa tgtgggggtt caatcggccg tagcccttta tatatataaa tgagagatct     540
gaacccgtta catgtcgttt accgagttaa tctcgtagat ttagctaaca aatcccacaa     600
gaaaatcgaa atcctaaccg attctacaca caagcggacc atccatgcca tcaccgcgga     660
tcatccggcc tagcgtcccc tgcccaaaag tgggctcaac aagcctaaat acatataatt     720
tataccacgt gcaacacatt tattcatcca tatcacatgt catgcaaggc ataagcatca     780
tgttaactta gttatactga catacattta tgagttgaga tgtccaggat gtgagcgcat     840
gagcccattg tccattcagg accaagacag gctactaagc actttctaca taacttgtat     900
gtgctaacta tagcatgctt atatggctct ctccaaagtt caaagctagc tcaaatcttt     960
tgatttaata aaacttaaat ttgtttgatt tcagataaac tgataatttt tataatattt    1020
agagtgagtt gaaaacagaa actggccgca aatccacctc aagccttttg atttgaccta    1080 aaaaaagaa gcccccacaa acaccactcc acactagtgc actgtctctc tccaaaggca    1140
```

```
gctgcattgg cctccagcct tttccctact gtgccgcgcg ccctcccttc tctctaatga    1200
tagcataggg agagaaggca tactccgagg catccttctc ctttccctct ccttccccaa    1260
acccttttcc tctttccctc gccccaagaa cttcatctca tctccaggcg ccctttttgc    1320
gcttgcgcag gaggagctca cggggacagt ggggcggaga gctcgatcgc tgctccacta    1380
tttcagtgga ggtccctccc caatccc                                        1407
```

<210> SEQ ID NO 2
<211> LENGTH: 1938
<212> TYPE: DNA
<213> ORGANISM: artificial sequence
<220> FEATURE:
<223> OTHER INFORMATION: The Zea mays KN1 gene promoter and Zea mays
      alcohol dehydrogenase I intron 6/Maize Streak Virus leader 1

<400> SEQUENCE: 2

```
ataaatttta caagtaaaaa agacttaact tggataaaaa aatgttttcg tggggcgggt      60
acatggggga acgtggacgg tcctcgtgaa actacgggga ttaaattttt ctccatttaa    120
atccccgcgg ggactaaatt agtctcatac ccatcccta  atagggaat  tttccgcggg    180 gaattgggga tcgagtcccc attgtcatct ctactctgcg cacgtctgga tggtcgcgcc    240
tggggcccga acggttcacg atggcgcaga gggtcttatt tttcacagca gacctagatc    300
ttgcctctcg ggagggatcc cgtcggggag gagagatcct agggtgtgtc ttggtgtcag    360
caggccaccc aagacgcttc taatcgatgt agaaccgaag aaatgcgaag atttaaggta    420
gaggaaggct aaactagagc tactcctaat acaaaatgta aaaacgataa gtaaatttga    480
tctgatcgaa tgtgggggtt caatcggccg tagcccttta tatatataaa tgagagatct    540
gaacccgtta catgtcgttt accgagttaa tctcgtagat ttagctaaca aatcccacaa    600
gaaaatcgaa atcctaaccg attctacaca caagcggacc atccatgcca tcaccgcgga    660
tcatccggcc tagcgtcccc tgcccaaaag tgggctcaac aagcctaaat acatataatt    720
tataccacgt gcaacacatt tattcatcca tatcacatgt catgcaaggc ataagcatca    780
tgttaactta gttatactga catacattta tgagttgaga tgtccaggat gtgagcgcat    840
gagcccattg tccattcagg accaagacag gctactaagc actttctaca taacttgtat    900
gtgctaacta tagcatgctt atatggctct ctccaaagtt caaagctagc tcaaatcttt    960
tgatttaata aaacttaaat ttgtttgatt tcagataaac tgataatttt tataatattt   1020
agagtgagtt gaaaacagaa actggccgca aatccacctc aagccttttg atttgaccta   1080
aaaaaaagaa gccccacaa  acaccactcc acactagtgc actgtctctc tccaaaggca   1140
gctgcattgg cctccagcct tttccctact gtgccgcgcg ccctcccttc tctctaatga   1200
tagcataggg agagaaggca tactccgagg catccttctc ctttccctct ccttccccaa   1260
acccttttcc tctttccctc gccccaagaa cttcatctca tctccaggcg ccctttttgc   1320
gcttgcgcag gaggagctca cggggacagt ggggcggaga gctcgatcgc tgctccacta   1380
tttcagtgga ggtccctccc caatccctg  aaggctcgac aaggcagtcc acggaggagc   1440
tgatatttgg tggacaagct gtggatagga gcaaccctat ccctaatata ccagcaccac   1500
caagtcaggc caatccccag atcacccag  cagattcgaa gaaggtacag tacacacaca   1560
tgtatatatg tatgatgtat cccttcgatc gaaggcatgc cttggtataa tcactgagta   1620 gtcatttat  tactttgttt tgacaagtca gtagttcatc catttgtccc attttttcag   1680
cttggaagtt tggttgcact ggccttggtc taataactga gtagtcattt tattacgttg   1740
```

-continued

```
tttcgacaag tcagtagctc atccatctgt cccattttt  cagctaggaa gtttggttgc   1800
actggccttg gactaataac tgattagtca ttttattaca ttgtttcgac aagtcagtag   1860
ctcatccatc tgtcccattt ttcagctagg aagttcggat ctggggccat tgttccagg   1920 cacgggataa gcattcag                                                 1938
```

<210> SEQ ID NO 3
<211> LENGTH: 4002
<212> TYPE: DNA
<213> ORGANISM: artificial sequence
<220> FEATURE:
<223> OTHER INFORMATION: Gene expression cassette containing the GUSPlus transgene that is driven by the Zea mays KN1 promoter, and flanked by Zea mays Peroxidase 5 3 'UTR

<400> SEQUENCE: 3

```
ataaattta  acaagtaaaa agacttaact tggataaaaa aatgttttcg tggggcgggt    60
acatggggga acgtggacgg tcctcgtgaa actacgggga ttaaatttt  ctccatttaa   120 atccccgcgg ggactaaatt agtctcatac ccatccccta ataggggaat tttccgcggg   180
gaattgggga tcgagtcccc attgtcatct ctactctgcg cacgtctgga tggtcgcgcc   240
tggggcccga acggttcacg atggcgcaga gggtcttatt tttcacagca gacctagatc   300
ttgcctctcg ggagggatcc cgtcggggag gagagatcct agggtgtgtc ttggtgtcag   360
caggccaccc aagacgcttc taatcgatgt agaaccgaag aaatgcgaag atttaaggta   420
gaggaaggct aaactagagc tactcctaat acaaaatgta aaaacgataa gtaaatttga   480
tctgatcgaa tgtgggggtt caatcggccg tagccccttta tatataaaa tgagagatct    540 gaacccgtta catgtcgttt accgagttaa tctcgtagat ttagctaaca aatcccacaa   600
gaaaatcgaa atcctaaccg attctacaca caagcggacc atccatgcca tcaccgcgga   660
tcatccggcc tagcgtcccc tgcccaaaag tgggctcaac aagcctaaat acatataatt   720
tataccacgt gcaacacatt tattcatcca tatcacatgt catgcaaggc ataagcatca   780
tgttaactta gttatactga catacattta tgagttgaga tgtccaggat gtgagcgcat   840
gagcccattg tccattcagg accaagacag gctactaagc actttctaca taacttgtat   900
gtgctaacta tagcatgctt atatggctct ctccaaagtt caaagctagc tcaaatcttt   960
tgatttaata aaacttaaat ttgtttgatt tcagataaac tgataatttt tataatattt  1020
agagtgagtt gaaaacagaa actggccgca aatccacctc aagcctttg  atttgaccta  1080 aaaaaaagaa gccccacaa  acaccactcc acactagtgc actgtctctc tccaaaggca  1140
gctgcattgg cctccagcct tttccctact gtgccgcgcg ccctccttc  tctctaatga  1200 tagcataggg agagaaggca tactccgagg catccttctc cttccctct  ccttcccaa   1260 acccttttcc tctttccctc gccccaagaa cttcatctca tctccaggcg ccctttttgc  1320
gcttgcgcag gaggagctca cggggacagt ggggcggaga gctcgatcgc tgctccacta  1380
tttcagtgga ggtccctccc caatcccgta cagtagttag ttgaggtacc ggatccacac  1440
gacaccatgg ttgatttgag ggtaaatttc tagttttttct ccttcatttt cttggttagg  1500
acccttttct cttttttattt ttttgagctt tgatctttct ttaaactgat ctattttta  1560 attgattggt tatggtgtaa atattacata gctttaactg ataatctgat tactttattt  1620
cgtgtgtcta tgatgatgat gatagttaca gaacagaagg acttccctgt accctatcaa  1680
cacagagaca aggggagttt tcgacttgaa tggtgtctgg aacttcaagc tggactacgg  1740
gaagggattg gaagagaagt ggtacgaaag caagttgaca gacactattt caatggccgt  1800
```

```
cccatcctcc tacaatgaca ttggcgtgac caaggaaatc agaaaccata tcggatatgt    1860
ctggtacgaa agggagttca cggtgccagc ttatctgaag gatcagcgta tcgtgcttag    1920
attcggctct gcaactcaca aagctattgt ctatgtcaat ggtgagctgg tcgttgagca    1980
caagggtgga ttcctgccct tcgaagctga atcaacaat tcactccgtg atggaatgaa    2040
tcgcgtcacc gttgccgtgg acaacatatt ggacgatagc accctcccgg ttgggctgta    2100
ctccgagagg catgaagagg gccttggaaa agtcattcgt aacaagccga actttgattt    2160
cttcaactat gctggcctgc accgtcctgt gaagatttat acgacccctt ttacgtacgt    2220
tgaggacatc tcagttgtga ccgacttcaa tggaccaacc gggactgtga cctatacggt    2280
ggactttcaa ggcaaggctg agaccgtgaa agtttccgtc gtggatgagg aaggcaaagt    2340
tgtcgcatcc acagagggcc ttagcggcaa cgtggagatt cctaatgtta tcctttggga    2400
accactgaac acgtatctct accagatcaa agtggaactt gttaatgacg gactgactat    2460
cgatgtctat gaagagccct tggggttag gactgtggaa gtcaacgatg gaagttcct    2520 catcaacaac aaaccttct acttcaaggg ctttggaaaa cacgaggaca ctcctatcaa    2580 cggcagagg tttaacgaag ctagcaatgt gatggatttc aacatactca aatggatcgg    2640
tgccaacagc ttcagaaccg cacactatcc ttactctgaa gagttgatgc gtcttgctga    2700
tcgcgagggt ctggtcgtta tagacgaaac tcctgctgtt ggcgtgcacc ttaacttcat    2760
ggccaccacc ggactcggtg aaggaagcga gagggtctca acctgggaga agattaggac    2820
gtttgagcac catcaagatg ttctcagaga acttgtgtca agagacaaga accatccatc    2880
tgtcgtgatg tggtcaatcg ccaacgaggc tgccactgag aagagggag cctacgagta    2940 cttcaagcca ttggtggagt tgacaaagga actcgacccc cagaagagac cggttacaat    3000
cgtgttgttc gtgatggcta cacctgagac ggacaaagtc gccgaactta ttgacgttat    3060
cgcactcaat cgctataacg gttggtactt cgatgggggt gatctcgaag cagctaaagt    3120
tcatcttaga caagaatttc acgcttggaa caagaggtgc cctggaaagc cgataatgat    3180
tactgagtac ggtgcagata ccgttgctgg gtttcacgac attgatccag ttatgttcac    3240
agaggaatat caagtcgagt actaccaagc aaatcacgtc gtgttcgatg agtttgagaa    3300
cttcgttggt gagcaggctt ggaacttcgc cgactttgcc acctctcaag gagtgatgcg    3360
cgtccaagga aacaagaagg gcgtgttcac tagagatcgc aagccaaagc tcgcagcaca    3420
cgtctttcgc gagcgctgga caaacattcc agattttggt tacaagaacg cttctcacca    3480
ccaccaccac cacgtttgag tagttagctt aatcacctaa tttaaataga gctctctacg    3540
agcaacacgt ccactaggat cagcagctgt cagtgacaga taagataacg gcgcaattac    3600
ctaatctgcg tagtacgagc agcggtaacc tttaaactga gggcactgaa gtcgcttgat    3660
gtgctgaatt gtttgtgatg ttggtggcgt attttgttta aataagtaag catggctgtg    3720 atttatcat atgatcgatc tttgggtt tatttaacac attgtaaaat gtgtatctat    3780
taataactca atgtataaga tgtgttcatt cttcggttgc catagatctg cttatttgac    3840
ctgtgatgtt ttgactccaa aaccaaaat cacaactcaa taaactcatg gaatatgtcc    3900 acctgttct tgaagagttc atctaccatt ccagttggca tttatcagtg ttgcagcggc    3960
gctgtgcttt gtaacataac aattgttacg gcatatatcc aa    4002
```

<210> SEQ ID NO 4
<211> LENGTH: 2673
<212> TYPE: DNA

<213> ORGANISM: artificial sequence
<220> FEATURE:
<223> OTHER INFORMATION: Gene expression cassette containing the aad-1 transgene that is driven by the Oryza sativa Actin1 promoter, and flanked by Zea mays Lipase 3' UTR

<400> SEQUENCE: 4

| | | | | |
|---|---|---|---|---|
| ctcgaggtca | ttcatatgct | tgagaagaga | gtcgggatag | tccaaaataa aacaaaggta | 60 |
| agattacctg | gtcaaaagtg | aaaacatcag | ttaaaaggtg | gtataaagta aaatatcggt | 120 |
| aataaaaggt | ggcccaaagt | gaaatttact | cttttctact | attataaaaa ttgaggatgt | 180 |
| ttttgtcggt | actttgatac | gtcattttg | tatgaattgg | ttttaagtt tattcgcttt | 240 |
| tggaaatgca | tatctgtatt | tgagtcgggt | tttaagttcg | tttgcttttg taaatacaga | 300 |
| gggatttgta | taagaaatat | ctttaaaaaa | acccatatgc | taatttgaca taattttga | 360 |
| gaaaaatata | tattcaggcg | aattctcaca | atgaacaata | ataagattaa aatagctttc | 420 |
| ccccgttgca | gcgcatgggt | atttttcta | gtaaaaataa | aagataaact tagactcaaa | 480 |
| acatttacaa | aaacaacccc | taaagttcct | aaagcccaaa | gtgctatcca cgatccatag | 540 |
| caagcccagc | caacccaac | ccaacccaac | ccaccccagt | ccagccaact ggacaatagt | 600 |
| ctccacaccc | cccactatc | accgtgagtt | gtccgcacgc | accgcacgtc tcgcagccaa | 660 |
| aaaaaaaaa | agaaagaaaa | aaaagaaaaa | gaaaaacag | caggtgggtc cgggtcgtgg | 720 |
| gggccggaaa | cgcgaggagg | atcgcgagcc | agcgacgagg | ccggccctcc ctccgcttcc | 780 |
| aaagaaacgc | ccccatcgc | cactatatac | atacccccc | ctctcctccc atcccccaa | 840 |
| ccctaccacc | accaccacca | ccacctccac | ctcctccccc | ctcgctgccg gacgacgcct | 900 |
| cccccctccc | cctccgccgc | cgccgcgccg | gtaaccaccc | cgcccctctc ctctttcttt | 960 |
| ctccgttttt | ttttccgtc | tcggtctcga | tctttggcct | tggtagtttg ggtgggcgag | 1020 |
| aggcggcttc | gtgcgcgccc | agatcggtgc | gcgggagggg | cgggatctcg cggctgggc | 1080 |
| tctcgccggc | gtgatccgg | cccggatctc | gcggggaatg | gggctctcgg atgtagatct | 1140 |
| gcgatccgcc | gttgttgggg | gagatgatgg | ggggtttaaa | atttccgcca tgctaaacaa | 1200 |
| gatcaggaag | aggggaaaag | ggcactatgg | tttatatttt | tatatatttc tgctgcttcg | 1260 |
| tcaggcttag | atgtgctaga | tcttttctttc | ttcttttgt | gggtagaatt tgaatccctc | 1320 |
| agcattgttc | atcggtagtt | tttcttttca | tgatttgtga | caaatgcagc ctcgtgcgga | 1380 |
| gcttttttgt | aggtagacca | tggctcatgc | tgccctcagc | cctctctccc aacgctttga | 1440 |
| gagaatagct | gtccagccac | tcactggtgt | ccttggtgct | gagatcactg gagtggactt | 1500 |
| gagggaacca | cttgatgaca | gcacctggaa | tgagatattg | gatgccttcc acacttacca | 1560 |
| agtcatctac | tttcctggcc | aagcaatcac | caatgagcag | cacattgcat tctcaagaag | 1620 |
| gtttggacca | gttgatccag | tgcctcttct | caagagcatt | gaaggctatc cagaggttca | 1680 |
| gatgatccgc | agagaagcca | atgagtctgg | aagggtgatt | ggtgatgact ggcacacaga | 1740 |
| ctccactttc | cttgatgcac | ctccagctgc | tgttgtgatg | agggcatag atgttcctga | 1800 |
| gcatggcgga | gacactgggt | tcctttcaat | gtacacagct | gggagacct tgtctccaac | 1860 |
| catgcaagcc | accatcgaag | ggctcaacgt | tgtgcactct | gccacacgtg tgttcggttc | 1920 |
| cctctaccaa | gcacagaacc | gtcgcttcag | caacacctca | gtcaaggtga tggatgttga | 1980 |
| tgctggtgac | agagagacag | tccatcccctt | ggttgtgact | catcctggct ctggaaggaa | 2040 |
| aggcctttat | gtgaatcaag | tctactgtca | gagaattgag | ggcatgacag atgcagaatc | 2100 |
| aaagccattg | cttcagttcc | tctatgagca | tgccaccaga | tttgacttca cttgccgtgt | 2160 |

```
gaggtggaag aaagaccaag tccttgtctg ggacaacttg tgcaccatgc accgtgctgt    2220
tcctgactat gctggcaagt tcagatactt gactcgcacc acagttggtg gagttaggcc    2280
tgcccgctga gtagttagct taatcaccta gagctcggtc gcagcgtgtg cgtgtccgtc    2340
gtacgttctg gccggccggg ccttgggcgc gcgatcagaa gcgttgcgtt ggcgtgtgtg    2400
tgcttctggt ttgctttaat tttaccaagt ttgtttcaag gtggatcgcg tggtcaaggc    2460
ccgtgtgctt taaagaccca ccggcactgg cagtgagtgt tgctgcttgt gtaggctttg    2520
gtacgtatgg gctttatttg cttctggatg ttgtgtacta cttgggtttg ttgaattatt    2580
atgagcagtt gcgtattgta attcagctgg gctacctgga cattgttatg tattaataaa    2640
tgctttgctt tcttctaaag atctttaagt gct                                 2673

<210> SEQ ID NO 5
<211> LENGTH: 7153
<212> TYPE: DNA
<213> ORGANISM: Zea mays

<400> SEQUENCE: 5
atggaggaga tcacccaaca ctttggagtt ggcgcaagca gccacggcca tggccacggc      60
cagcaccacc atcatcacca ccaccaccac ccgtgggcat cctccctcag cgccgtcgta     120
gcgccgctgc cgccgcaacc gccaagcgca ggcctgccgc tgaccctgaa cacggtggcg     180
gccactggga acagcggcgg tagcggcaac ccggtgctgc agcttgccaa cggtggcggc     240
ctcctcgacg catgcgtcaa ggcgaaggag ccctcgtcgt cgtctcccta cgcaggcgac     300
gtcgaggcca tcaaggccaa gatcatctcg cacccacact actactcgct cctcactgcc     360
tacctcgagt gcaacaaggc aagcaagact agtagccgca gtctaacaat agctctcctg     420
cttccggttc agctactgct gctagcgaag tttggccaca tctgatgtca agagcatggc     480
gcatgcacat actttctgct tgcttttaca tagcatacta tagtttatgc atgctgctca     540
tgtagacatg tgcatctggt gttcggaact ttctcaaacg gccgtgggtg tttgcaggtg     600
ggggcaccac cggaggtgtc ggcgaggctg acggagatag cgcaggaggt ggaggcgcgg     660
cagcgcacgg cgctcggcgg cctggccgct gcgacggagc cggagctgga ccagttcatg     720
gtgaggcatc tttaggttta tttcacgcgc gcgcagcgca ccattattag tcgttttcag     780
ctcgggctcg gatttaattt gcgtgtatat atggtaggag gcgtaccacg agatgctggt     840
gaagttcagg gaggagctga cgaggccgct gcaggaggcg atggagttca tgcgaagggt     900
ggagtcgcag ctgaactcgc tttccatctc cggaaggtcg ctgcgcaaca tcctttcatc     960
tggtactgaa gttgctgcgg cccatgcccc tcttatttta tattagatga tttcttggat    1020
cggttgtcgc ctcatgcagc gatgcatgcc ctccctcttg ttaaaatctt cctgtcctct    1080
ccttcgtctt gctgtcctct ttcttggttg agcatatgtt gatgggtttt ttttttttgca    1140 tttcaaaagg gttaaattt tccttgatgt ggttctcag caattaattt tggcatctgt    1200
gtagttccct ttttaagagc atcttgctat gcatgcatat tttgagtata gatagctgcg    1260
gaacgcagat gaatgtcttg tctgcgcttc atgttttta atgcgcggca gcattcctaa    1320
tcaggggttt cgaaagagaa tcttctccct gcttgctttt cctggccatg catctgtgag    1380
attcttctct ctggcttccg tcgatctttg cttctgctgg aaaggaaata gtcctcagtc    1440
acacatgtgc aggagcgcag cttcaatcta gcatggctga aagctctctg gttctttcca    1500
tacactccat cctgcacatt ccttgcatat attctgctgt taaactgctt agcgacgagg    1560
```

-continued

```
atgaatgaaa acacctgtct tttttactag tgggagtact aatttggctg ctgttgccat    1620
ggatgcgttg ttcatcgtcc tccattatat tgatcgattc catttggaat ggaacatgtg    1680
catgtgttct gcgagtagtt cctggctcag cgcagccatc ttttcccatg atgggaaccc    1740
cagggagttc ccttgttcta gggtttggga aagggccaca gtgtactggg tgctgtggca    1800
ttgtgcaagc acagtctata gccgaggagt ctcactggcg tatgtcagtg aaacatagta    1860
gtatacacgt tgtagtagtg ggagatcaga gagagagaga gatggggagt catccccat     1920
ctgtcacgca agcttgtggc cagaacattc ttgtcatctt tctcccctc aagagatgta     1980
gctacctgtt gtcctagaat ctatagtgtt gtggtgtggt cttccaggtg cgcacacaga    2040
tctggccact gctggcctta gtatttgcta attttaaaat gaacacatca ggtagatcga    2100
gacgatccat ggcaagcgtc tttctaatga cctatcacaa ggctatagta acaactcgta    2160
ccaccacagt tacgcacagc ccagagtttt tcacttctcg gttctgttct tcttagagca    2220
ctggctatgg ctagtatata tgcatggcag caacacacac acacacacac aatcacttca    2280
ttactggagc aagttagcga agaagctgcc atctgatgtc gtagaatgct gcaaaaatga    2340
aaggttcaga ggcaggcata cgggttgaaa tggagcaccg tatgcggcgg cccagttttt    2400
tgtgttctga ccggcgcagt ggacaaaatg gcctgtgtgc ctcgagaacc atagagacag    2460
ttgcctagcg catgagcgct gagcggcccc tattatttga tgtgagatct ctctatcaat    2520
ggatgtgtga tctgctaggt ttatattata tatgcgtcta ctatatccct accagtccct    2580
gtattttctg acagatagac ttctccccg cgcgttctct cataaataaa tgacggtcaa     2640
ggaacattgg atgctttccg aggcgagcta gtacaagttt catctgcgtt tgcgtttgta    2700
ttttttcagct gtcaactcag atttctcctc agctccaact gttctttgac cttcttggta   2760
ctgttttctt ggaagaaact atttgttgac cattttttggt tataataagg ccacagacaa   2820
actgttgaat ttaatcacaa aacaacacta ctgcgttttt tctttttcttt tctgactgat   2880
gttgcacatg tactccaaga ttcttggttg catgcactct ttcaaggtca tgcaaaagca    2940
gggacaccgg gtgtcacgag tttccgtttg tctcgaggta agaccaaaaa agataccgga    3000
agcaaacaac ataaaacaaa gggtaggatg gaaaagagct gatggatttt acaatgtatc    3060
gccagagtgg aaaagacaac gcgactagag gaaaggaacg atctggcact tccaactgtg    3120
tgaattcttc catttgatgt gcgtctcgtg catgttatt ttcttggtta ctggaaatcg      3180
ggtgcatcca ttttttattca ggattcaatt attggttact ggagccaggt ccgttcgttt    3240
ttattttcct tttgagattg actggatcga ttctctggtt ctagtcactt atgctgttgg    3300
ttttatcgtt ttcatggatt tctattctat ctctcccaat attcagtatc acataaaatc    3360
ctgtgactag attcttttat cacatacaat cttgtttttt tattttcttt aatttaacac    3420
tggatttgtt tgataatatg ttctgaaaaa cgttaataaa tttaagcaca acagccttt     3480
aaaaatatgt ataattattt accttgaaac ccagcatcgg ccgggaacaa ggaaaagaac    3540
tcaaggtttt aaatgcattg aaatgaaaca ttaatggagt gtttggtttg aataatgatg    3600
tagtccatca tcttctcact cctcactttt tgtttggtt tatggaatgg agtgagttaa     3660
tccatcaaca cctcattcct catagttagt tgtttagtac taatatgtgg aatgaagtca    3720
tcccaccaaa tttgaagaat ggactcatga tgcaccactt cattttagat agagtgattc    3780
atcaaaccaa acacctcata agggcatgtt tggatcctag gagctaaaag aaaagtgact    3840
aaagtttagt cactttagga gctaaagatc tactaaatag gaaactaaaa gtgactagaa    3900
tagtaaaagg tatcttttta gtcattttta gctcctaaga aggagctaaa ttttagttag    3960
```

```
tttggtttag ctcttggatc caaacaggcc ctaagaaaat gtttcgacaa catttgggac    4020
aataaaacag ttcctaagga tttctttggc aagattaggc cttctttgga acaaagaaaa    4080
atgaaggaat cttgaaggat tgaaatccta taggaagctt tcatatgcaa agaattgtgt    4140
tcctaggatg atttctaaca agaggctcat cccttgaaa attgttcttt gtgtctatct     4200
ctctcctcta attcatgtgt tcttatgttg cattgaaaca ctattagaaa attttcatgt    4260
gttttaattt atgtatgatt gtaagtgtca agcagcacta ttcctacatt ttttctattc    4320
ctgtgtttta tcgatactgc atcccaatga aggcctaagc gtatcatgca atcttttcca    4380
gaagtttttt agattgctgt ataatgacaa ggtgcaatgc tcttcgtttt cttttttggt    4440
tttcctcatt ttcagcaagg ccaccaaatt tttccatgat gttcttgtct tattcctgta    4500
gtatccctcg aaaaaatttc atagctttct acatccatgt tatctaatga tgttcttcat    4560
ttcaaagaca gacacatttg gcataagttc tgattggtca ctaaaacttt gtggtacggt    4620
catttacttt tactatacac atgtactgta ttcatgcgta cattgtactt tgtccattgg    4680
ggcctttcct ctttttaata caacgggcat cgtttcaaaa aaaatgtgtc agtcgtaact    4740
gcacacttct ttagttttcc ccagttaaca gcatgacgga atagagttac agagtctcat    4800
gtcaagtcac atatatcctc aagtcgtttc taaaattaaa gtaatatttt cattgttgct    4860
tccgtaagaa tgcaccacaa acacaaaata tcatttcctt tatgcaaata tatatatg      4920 aatgtttgtt tctggcagtg gtgagaagct tctcactgag ccaaaggttt tagggatgcc    4980
atgtgctctt tttctttttt aagtgtagat taagcaaacc tttataattt ttaaactcca    5040
accagatacc ttttctaaat tcataaatgc tctggactat cttcacgaaa aaggctttgg    5100
taatatgttc acaagcctcc tttatctgtt atcctgggct agacatagga tgtgttgaag    5160
caatacaagc ggagttgttt cgttaaagca aaaaaaaaac tgtaacttta tattggagaa    5220
tatacatcgt tctcccatat ttgttacagt gctcataaat agacaaagtt ttttttttga    5280
aatcttaagc cctgtgtttc tttggttatc ttatctctat attgcttcca aatatgttgt    5340
catcaagatg gatatagata attgtcaaaa cgaaaagtgt gcatggttca tttatgccaa    5400
ttctgaaaag cataagttaa atattaagat accaataaag aaaaacatat gcagtgttga    5460
ctgttgggaa aagaacaagg tctgcacata cacttgcaat ataaatcttt ttacccagca    5520
ataaaaaaac gatcaaatat cacgcaaaca agtaatacg tccagaaaca cccatactt      5580 tgaaattcgt ctttgaaatg cagtaggttc acaaaataaa atggtgcaac tgcacatgtc    5640
ctttatatct gtactcaatg ggttttctgg agatgttaga ttgattggtg ggacaatatc    5700
ctaatgcaac tcgcaaattc ccaaggccga actcaagtgg gagtttggat gattttttt    5760 gtaaagaagc agatggctgc gctagtttac atagaccatc acacttcaca attcacattc    5820
atgaagtcat aactttgttc acttcttgtt taactatggc atataaaaac atactgtgtg    5880
ttgttttgct tgtatggaac atgtattta gttttttagt aaataagttc agtaaatgtc     5940
tttgccggac aaatttcacc aatctggcta cgaatgatgc ttgatcactt cttttgtttt    6000
atctaaaagt tccatgtctt atgcttgaag gctcttctga ggaggatcaa gaaggtagcg    6060
gaggagagac cgagctccct gaagttgatg cacatggtgt ggaccaagag ctgaagcacc    6120
atctcctgaa gaaatacagt ggctatctaa gctcgctcaa gcaagaactg tcaaagaaga    6180
agaagaaagg gaagctcccc aaggaggctc gccagcagct ccttagctgg tgggatcagc    6240
actacaaatg gccttacccc tcagtacgtc ttctttttat tcttccattt taactattgt    6300
```

-continued

```
tggtgacaca tgatttagac gatgccaatt cttcatgaac ttttcatagc cagctaccca      6360
atgttagtac tgactgcaca ttgtaattca agggtaagta tatatataca taaatcacat      6420
ttggcaaatc taagctacat atgggtcttt gatcttccat gacggtctgt tgatctctga      6480
tttgcatatc ggcatataaa aagtgagcca aaatatgtca gagtctaata atattgatca      6540
gggagtggca ggtgattatt ggtattaatt taaccttatt taaggtattt tgaaacttct      6600
gtagcgttct tactaaatac cattgatttt aatttaagca actatatatt tatctggtga      6660
aaaatgaagc cttttctgat atacaaattg aagagtctac aatggtttca cttacatggc      6720
tgaaacagaa aatcatagtg ccctgaattg tgtgttgata ctcataagcg cagattcaaa      6780
tttgtaattt tcaagtttag ggttctaagt gaaaaaaaaa cattgagtcc aggagcatac      6840
actgaacttt ttttttatca tatcttcatt ttgttggatg ttttgtatac ggcatatagc      6900
ctgtgcttcc ctactggata tgaattaacc aactcttccc atcggtgagc aggagactca      6960
gaaggtggca ctggctgagt ctaccgggct tgacctgaag cagatcaaca actggttcat      7020
caaccagcgg aagcggcact ggaagccatc cgaggagatg caccacctga tgatggacgg      7080
gtaccacacc accaatgcct tctacatgga cggccacttc atcaacgacg gcgggctgta      7140
ccggctcggc tag                                                        7153

<210> SEQ ID NO 6
<211> LENGTH: 4533
<212> TYPE: DNA
<213> ORGANISM: artificial sequence
<220> FEATURE:
<223> OTHER INFORMATION: Gene expression cassette containing the GUSPlus
      transgene that is driven by the Zea mays KN1 promoter fusion with
      the Zea mays alcohol dehydrogenase I intron 6/Maize Streak Virus
      leader 1, and flanked by Zea mays Peroxidase 5 3'UTR

<400> SEQUENCE: 6 ataaattta acaagtaaaa agacttaact tggataaaaa aatgttttcg tggggcgggt       60 acatgggga acgtggacgg tcctcgtgaa actacgggga ttaaattttt ctccatttaa      120
atccccgcgg ggactaaatt agtctctatac ccatccccta ataggggaat tttccgcggg    180
gaattgggga tcgagtcccc attgtcatct ctactctgcg cacgtctgga tggtcgcgcc    240
tggggcccga acggttcacg atggcgcaga gggtcttatt tttcacagca gacctagatc    300
ttgcctctcg ggagggatcc cgtcggggag gagagatcct agggtgtgtc ttggtgtcag    360
caggccaccc aagacgcttc taatcgatgt agaaccgaag aaatgcgaag atttaaggta    420
gaggaaggct aaactagagc tactcctaat acaaaatgta aaaacgataa gtaaatttga    480
tctgatcgaa tgtgggggtt caatcggccg tagccctta tatatataaa tgagagatct      540
gaacccgtta catgtcgttt accgagttaa tctcgtagat ttagctaaca aatcccacaa    600
gaaaatcgaa atcctaaccg attctacaca caagcggacc atccatgcca tcaccgcgga   660
tcatccggcc tagcgtcccc tgcccaaaag tgggctcaac aagcctaaat acatataatt    720
tataccacgt gcaacacatt tattcatcca tatcacatgt catgcaaggc ataagcatca    780
tgttaactta gttatactga catacattta tgagttgaga tgtccaggat gtgagcgcat    840
gagcccattg tccattcagg accaagacag gctactaagc actttctaca taacttgtat    900
gtgctaacta tagcatgctt atatggctct ctccaaagtt caaagctagc tcaaatcttt    960
tgatttaata aaacttaaat ttgtttgatt tcagataaac tgataatttt tataatattt    1020
agagtgagtt gaaaacagaa actggccgca aatccacctc aagccttttg atttgaccta    1080
```

```
aaaaaaagaa gcccccacaa acaccactcc acactagtgc actgtctctc tccaaaggca    1140
gctgcattgg cctccagcct tttccctact gtgccgcgcg ccctcccttc tctctaatga    1200
tagcataggg agagaaggca tactccgagg catccttctc ctttccctct ccttccccaa    1260
acccttttcc tctttccctc gccccaagaa cttcatctca tctccaggcg cccttttgc     1320
gcttgcgcag gaggagctca cggggacagt ggggcggaga gctcgatcgc tgctccacta    1380
tttcagtgga ggtccctccc caatcccctg aaggctcgac aaggcagtcc acggaggagc    1440
tgatatttgg tggacaagct gtggatagga gcaaccctat ccctaatata ccagcaccac    1500
caagtcaggg caatcccag atcaccccag cagattcgaa gaaggtacag tacacacaca     1560
tgtatatatg tatgatgtat cccttcgatc gaaggcatgc cttggtataa tcactgagta    1620
gtcattttat tactttgttt tgacaagtca gtagttcatc catttgtccc attttttcag    1680
cttggaagtt tggttgcact ggccttggtc taataactga gtagtcattt tattacgttg    1740
tttcgacaag tcagtagctc atccatctgt cccattttt cagctaggaa gtttggttgc     1800
actggccttg gactaataac tgattagtca ttttattaca ttgtttcgac aagtcagtag    1860
ctcatccatc tgtcccattt ttcagctagg aagttcggat ctgggccat ttgttccagg     1920
cacgggataa gcattcaggt acagtagtta gttgaggtac cggatccaca cgacaccatg    1980
gttgatttga gggtaaattt ctagttttc tccttcattt tcttggttag gaccctttc      2040
tcttttatt ttttgagct tgatctttc tttaaactga tctatttttt aattgattgg       2100
ttatggtgta aatattacat agctttaact gataatctga ttactttatt tcgtgtgtct    2160
atgatgatga tgatagttac agaacagaag gacttccctg tacctatca acacagagac     2220
aaggggagtt ttcgacttga atggtgtctg gaacttcaag ctggactacg gaagggatt     2280
ggaagagaag tggtacgaaa gcaagttgac agacactatt tcaatggccg tcccatcctc    2340
ctacaatgac attggcgtga ccaaggaaat cagaaaccat atcggatatg tctggtacga    2400
aagggagttc acggtgccag cttatctgaa ggatcagcgt atcgtgctta gattcggctc    2460
tgcaactcac aaagctattg tctatgtcaa tggtgagctg gtcgttgagc acaagggtgg    2520
attcctgccc ttcgaagctg aaatcaacaa ttcactccgt gatggaatga atcgcgtcac    2580
cgttgccgtg gacaacatat tggacgatag caccctcccg gttgggctgt actccgagag    2640
gcatgaagag ggccttggaa aagtcattcg taacaagccg aactttgatt tcttcaacta    2700
tgctggcctg caccgtcctg tgaagattta tacgaccct tttacgtacg ttgaggacat     2760
ctcagttgtg accgacttca atggaccaac cgggactgtg acctatacgg tggactttca    2820
aggcaaggct gagaccgtga agtttccgt cgtggatgag gaaggcaaag ttgtcgcatc     2880
cacagagggc cttagcggca acgtggagat tcctaatgtt atcctttggg aaccactgaa    2940
cacgtatctc taccagatca aagtggaact tgttaatgac ggactgacta tcgatgtcta    3000
tgaagagccc tttggggtta ggactgtgga agtcaacgat gggaagttcc tcatcaacaa    3060
caaacccttc tacttcaagg ctttggaaa acacagggac actcctatca acggcagagg     3120
ctttaacgaa gctagcaatg tgatggattt caacatactc aaatggatcg gtgccaacag    3180
cttcagaacc gcacactatc cttactctga gagttgatg cgtcttgctg atcgcgaggg     3240
tctggtcgtt atagacgaaa ctcctgctgt tggcgtgcac cttaacttca tggccaccac    3300
cggactcggt gaaggaagcg agagggtctc aacctgggag aagattagga cgtttgagca    3360
ccatcaagat gttctcagag aacttgtgtc aagagacaag aaccatccat ctgtcgtgat    3420
gtggtcaatc gccaacgagg ctgccactga ggaagaggga gcctacgagt acttcaagcc    3480
```

```
attggtggag ttgacaaagg aactcgaccc ccagaagaga ccggttacaa tcgtgttgtt    3540
cgtgatggct acacctgaga cggacaaagt cgccgaactt attgacgtta tcgcactcaa    3600
tcgctataac ggttggtact tcgatggggg tgatctcgaa gcagctaaag ttcatcttag    3660
acaagaattt cacgcttgga acaagaggtg ccctggaaag ccgataatga ttactgagta    3720
cggtgcagat accgttgctg ggtttcacga cattgatcca gttatgttca cagaggaata    3780
tcaagtcgag tactaccaag caaatcacgt cgtgttcgat gagtttgaga acttcgttgg    3840
tgagcaggct tggaacttcg ccgactttgc cacctctcaa ggagtgatgc gcgtccaagg    3900
aaacaagaag ggcgtgttca ctagagatcg caagccaaag ctcgcagcac acgtcttccg    3960
cgagcgctgg acaaacattc agattttggt tacaagaac gcttctcacc accaccacca    4020
ccacgtttga gtagttagct taatcaccta atttaaatag agctctctac gagcaacacg    4080
tccactagga tcagcagctg tcagtgacag ataagataac ggcgcaatta cctaatctgc    4140
gtagtacgag cagcggtaac ctttaaactg agggcactga agtcgcttga tgtgctgaat    4200
tgtttgtgat gttggtggcg tattttgttt aaataagtaa gcatggctgt gattttatca    4260
tatgatcgat ctttggggtt ttatttaaca cattgtaaaa tgtgtatcta ttaataactc    4320
aatgtataag atgtgttcat tcttcggttg ccatagatct gcttatttga cctgtgatgt    4380
tttgactcca aaaccaaaa tcacaactca ataaactcat ggaatatgtc cacctgtttc    4440
ttgaagagtt catctaccat tccagttggc atttatcagt gttgcagcgg cgctgtgctt    4500
tgtaacataa caattgttac ggcatatatc caa                                 4533

<210> SEQ ID NO 7
<211> LENGTH: 372
<212> TYPE: DNA
<213> ORGANISM: zea mays

<400> SEQUENCE: 7
ccccagcaga ttcgaagaag gtacagtaca cacacatgta tatatgtatg atgtatccct      60
tcgatcgaag gcatgccttg gtataatcac tgagtagtca ttttattact ttgttttgac    120
aagtcagtag ttcatccatt tgtcccattt tttcagcttg gaagtttggt tgcactggcc    180
ttggtctaat aactgagtag tcattttatt acgttgtttc gacaagtcag tagctcatcc    240
atctgtccca ttttttcagc taggaagttt ggttgcactg gccttggact aataactgat    300
tagtcatttt attacattgt ttcgacaagt cagtagctca tccatctgtc cattttttca    360
gctaggaagt tc                                                         372

<210> SEQ ID NO 8
<211> LENGTH: 531
<212> TYPE: DNA
<213> ORGANISM: artificial sequence
<220> FEATURE:
<223> OTHER INFORMATION: Zea mays alcohol dehydrogenase I intron 6 /
      Maize Streak Virus leader 1 fusion polynucleotide sequence

<400> SEQUENCE: 8
ctgaaggctc gacaaggcag tccacggagg agctgatatt tggtggacaa gctgtggata      60
ggagcaaccc tatccctaat ataccagcac caccaagtca gggcaatccc cagatcaccc    120
cagcagattc gaagaaggta cagtacacac acatgtatat atgtatgatg tatcccttcg    180
atcgaaggca tgccttggta taatcactga gtagtcattt tattactttg ttttgacaag    240
tcagtagttc atccatttgt cccatttttt cagcttggaa gtttggttgc actggccttg    300
```

-continued

```
gtctaataac tgagtagtca ttttattacg ttgtttcgac aagtcagtag ctcatccatc    360
tgtcccattt tttcagctag gaagtttggt tgcactggcc ttggactaat aactgattag    420
tcattttatt acattgtttc gacaagtcag tagctcatcc atctgtccca tttttcagct    480
aggaagttcg gatctggggc catttgttcc aggcacggga taagcattca g             531
```

PLANT PROMOTER FOR TRANSGENE EXPRESSION

CROSS REFERENCE TO RELATED APPLICATION

The present application claims priority to the benefit of U.S. Provisional Patent Application Ser. No. 62/244,843 filed Oct. 22, 2015 the disclosure of which is hereby incorporated by reference in its entirety.

INCORPORATION BY REFERENCE OF MATERIAL SUBMITTED ELECTRONICALLY

Incorporated by reference in its entirety is a computer-readable nucleotide/amino acid sequence listing submitted concurrently herewith and identified as follows: one 30.7 KB ACII (Text) file named "77670-US-PSP-20151021-Sequence-Listing-ST25.txt" created on Oct. 21, 2015.

BACKGROUND

Many plant species are capable of being transformed with transgenes to introduce agronomically desirable traits or characteristics. The resulting plant species are developed and/or modified to have particular desirable traits. Generally, desirable traits include, for example, improving nutritional value quality, increasing yield, conferring pest or disease resistance, increasing drought and stress tolerance, improving horticultural qualities (e.g., pigmentation and growth), imparting herbicide tolerance, enabling the production of industrially useful compounds and/or materials from the plant, and/or enabling the production of pharmaceuticals.

Transgenic plant species comprising multiple transgenes stacked at a single genomic locus are produced via plant transformation technologies. Plant transformation technologies result in the introduction of a transgene into a plant cell, recovery of a fertile transgenic plant that contains the stably integrated copy of the transgene in the plant genome, and subsequent transgene expression via transcription and translation results in transgenic plants that possess desirable traits and phenotypes. However, novel gene regulatory elements that allow the production of transgenic plant species to highly express multiple transgenes engineered as a trait stack are desirable.

Likewise, novel gene regulatory elements that allow the expression of a transgene within particular tissues or organs of a plant are desirable. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Furthermore, it may be desirable to express a transgene in leaf and stem tissues of a plant to provide tolerance against herbicides, or resistance against above ground insects and pests.

Therefore, a need exists for new gene regulatory elements that can drive the desired levels of expression of transgenes in specific plant tissues.

BRIEF SUMMARY

In embodiments of the subject disclosure, the disclosure relates to a nucleic acid vector comprising a promoter operably linked to a polylinker sequence; a non-*Zea mays* KN1 gene; or a combination of the polylinker sequence and the non-*Zea mays* KN1 gene, wherein said promoter comprises a polynucleotide sequence that has at least 90% sequence identity with SEQ ID NO: 1. In an embodiment, the promoter is 1,407 bp in length. In other embodiments, the promoter consists of a polynucleotide sequence that has at least 90% sequence identity with SEQ ID NO: 1. Furthermore, the above described embodiments comprise a sequence encoding a selectable maker. In further embodiments, the promoter is operably linked to a transgene. Accordingly, the transgene encodes a selectable marker or a gene product conferring insecticidal resistance, herbicide tolerance, nitrogen use efficiency, water use efficiency, expression of an RNAi, or nutritional quality. In other embodiments, the nucleic acid vector further comprises a 3' untranslated polynucleotide sequence. In additional embodiments, the nucleic acid vector further comprises a 5' untranslated polynucleotide sequence. In further embodiments, the nucleic acid vector further comprises an intron sequence. In an embodiment, the promoter has reproductive meristematic tissue specific expression.

In embodiments of the subject disclosure, the disclosure relates to a transgenic plant comprising a polynucleotide sequence that has at least 90% sequence identity with SEQ ID NO:1 operably linked to a transgene. In embodiments, the plant is selected from *Zea mays*, wheat, rice, sorghum, oats, rye, bananas, sugar cane, soybean, cotton, *Arabidopsis*, tobacco, sunflower, and canola. In an embodiment the transgene is inserted into the genome of the transgenic plant. In such an embodiment, the promoter comprises a polynucleotide sequence having at least 90% sequence identity with SEQ ID NO:1 and said promoter is operably linked to a transgene. In further embodiments, the transgenic plant further comprises a 3' untranslated sequence. In an embodiment, the transgene has reproductive meristematic tissue specific expression. In another embodiment, the promoter is 1,407 bp in length.

In embodiments of the subject disclosure, the disclosure relates to a method for producing a transgenic plant cell, the method comprising the steps of transforming a plant cell with a gene expression cassette comprising a *Zea mays* KN1 promoter operably linked to at least one polynucleotide sequence of interest, isolating the transformed plant cell comprising the gene expression cassette, and producing a transgenic plant cell comprising the *Zea mays* KN1 promoter operably linked to at least one polynucleotide sequence of interest. In further embodiments, the plant is transformed using a transformation method. The transformation method may be selected from any of the following methods; an *Agrobacterium*-mediated transformation method, a biolistics transformation method, a silicon carbide transformation method, a protoplast transformation method, and a liposome transformation method. In embodiments, the polynucleotide sequence of interest is constitutively expressed throughout the transgenic plant cell. In other embodiments, the polynucleotide sequence of interest is stably integrated into the genome of the transgenic plant cell. Further steps of transforming a plant cell include regenerating the transgenic plant cell into a transgenic plant, and obtaining the transgenic plant, wherein the transgenic plant comprises the gene expression cassette comprising the *Zea mays* KN1 promoter of claim 1 operably linked to at least one polynucleotide sequence of interest. In embodiments, the *Zea mays* KN1 promoter comprises the polynucleotide of SEQ ID NO:1. In other embodiments, the *Zea mays* KN1 promoter is operably linked to a first polynucleotide sequence of interest operably linked to the 3' end of SEQ ID NO:1. In an embodiment, the transgenic plant cell is a monocotyledonous transgenic plant cell or a dicotyledonous transgenic plant cell. Examples of dicotyledonous transgenic plant cells include an *Arabidopsis* plant cell, a tobacco plant cell, a soybean plant cell, a canola plant cell, and a cotton plant cell. Examples of monocotyledonous transgenic plant cells include a *Zea mays* plant cell, a rice plant cell, and a wheat plant cell.

In embodiments of the subject disclosure, the disclosure relates to a method for expressing a polynucleotide sequence of interest in a plant cell, the method comprising introducing into the plant cell a polynucleotide sequence of interest operably linked to a *Zea mays* KN1 promoter. In embodiments, the polynucleotide sequence of interest operably linked to the *Zea mays* KN1 promoter is introduced into the plant cell by a plant transformation method. Examples of such a plant transformation method include an *Agrobacterium*-mediated transformation method, a biolistics transformation method, a silicon carbide transformation method, a protoplast transformation method, and a liposome transformation method. In further embodiments, the polynucleotide sequence of interest is expressed by the *Zea mays* KN1 promoter in reproductive meristematic tissue. In additional embodiments, the polynucleotide sequence of interest is stably integrated into the genome of the plant cell. In such embodiments, the transgenic plant cell is a monocotyledonous plant cell or a dicotyledonous plant cell. Examples of dicotyledonous plant cells include an *Arabidopsis* plant cell, a tobacco plant cell, a soybean plant cell, a canola plant cell, and a cotton plant cell. Examples of monocotyledonous plant cells include a *Zea mays* plant cell, a rice plant cell, and a wheat plant cell.

In embodiments of the subject disclosure, the disclosure relates to a transgenic plant cell comprising a *Zea mays* KN1 promoter. In an embodiment, the transgenic plant cell comprises a transgenic event. In other embodiments, the transgenic event comprises an agronomic trait. Examples of an agronomic trait include an insecticidal resistance trait, herbicide tolerance trait, nitrogen use efficiency trait, water use efficiency trait, nutritional quality trait, DNA binding trait, selectable marker trait, small RNA trait, or any combination thereof. In some embodiments, the herbicide tolerant trait comprises an aad-1 coding sequence. In further embodiments, the transgenic plant cell produces a commodity product. Examples of commodity products include protein concentrate, protein isolate, grain, meal, flour, oil, or fiber. In further embodiments, the transgenic plant cell is selected from the group consisting of a dicotyledonous plant cell or a monocotyledonous plant cell. In some embodiments the transgenic plant cell is a *Zea mays* plant cell. In additional embodiments, the *Zea mays* KN1 promoter comprises a polynucleotide with at least 90% sequence identity to the polynucleotide of SEQ ID NO:1. In other embodiments, the *Zea mays* KN1 promoter is 1,407 bp in length. In further embodiments, the *Zea mays* KN1 promoter consists of SEQ ID NO:1. In an embodiment, a first polynucleotide sequence of interest is operably linked to the 3' end of SEQ ID NO:1. In embodiments, the agronomic trait is expressed reproductive meristematic tissue.

In embodiments of the subject disclosure, the disclosure relates to an isolated polynucleotide comprising a nucleic acid sequence with at least 90% sequence identity to the polynucleotide of SEQ ID NO:1. In further embodiments, the isolated polynucleotide comprising a nucleic acid sequence with at least 90% sequence identity to the polynucleotide of SEQ ID NO:1 drives reproductive meristematic tissue specific expression. Regarding such an embodiment, the expression activity occurs within a plant cell. In another embodiment, an open-reading frame polynucleotide coding for a polypeptide and a termination sequence are operably linked to the isolated polynucleotide comprising a nucleic acid sequence with at least 90% sequence identity to the polynucleotide of SEQ ID NO:1. In further embodiments, the isolated polynucleotide comprising a nucleic acid sequence with at least 90% sequence identity to the polynucleotide of SEQ ID NO:1 comprises a sequence of 1,407 bp in length.

The foregoing and other features will become more apparent from the following detailed description of several embodiments.

DETAILED DESCRIPTION

I. Overview of Several Embodiments

Development of transgenic plant products is becoming increasingly complex. Commercially viable transgenic plants now require the stacking of multiple transgenes into a single locus. Plant promoters and 3' UTRs used for basic research or biotechnological applications are generally uni-directional, directing only one gene that has been fused at its 3' end (downstream) for the promoter, or at its 5' end (upstream) for the 3' UTR. Accordingly, each transgene usually requires a promoter and 3' UTR for expression, wherein multiple regulatory elements are required to express multiple transgenes within one gene stack. With an increasing number of transgenes in gene stacks, the same promoter and/or 3' UTR is routinely used to obtain optimal levels of expression patterns of different transgenes. Obtaining optimal levels of transgene expression is necessary for the production of a single polygenic trait. Unfortunately, multi-gene constructs driven by the same promoter and/or 3' UTR are known to cause gene silencing resulting in less efficacious transgenic products in the field. The repeated promoter and/or 3' UTR elements may lead to homology-based gene silencing. In addition, repetitive sequences within a transgene may lead to gene intra locus homologous recombination resulting in polynucleotide rearrangements. The silencing and rearrangement of transgenes will likely have an undesirable affect on the performance of a transgenic plant produced to express transgenes. Further, excess of transcription factor (TF)-binding sites due to promoter repetition can cause depletion of endogenous TFs leading to transcriptional inactivation. Given the need to introduce multiple genes into plants for metabolic engineering and trait stacking, a variety of promoters and/or 3' UTRs are required to develop transgenic crops that drive the expression of multiple genes.

A particular problem in promoter and/or 3' UTR identification is the need to identify tissue-specific promoters, related to specific cell types, developmental stages and/or functions in the plant that are not expressed in other plant tissues. Tissue specific (i.e., tissue preferred) or organ specific promoters drive gene expression in a certain tissue such as in the kernel, root, leaf, or tapetum of the plant. Tissue and developmental stage specific promoters and/or 3' UTRs can be initially identified from observing the expression of genes, which are expressed in particular tissues or at particular time periods during plant development. These tissue specific promoters and/or 3' UTRs are required for certain applications in the transgenic plant industry and are desirable as they permit specific expression of heterologous genes in a tissue and/or developmental stage selective manner, indicating expression of the heterologous gene differentially at various organs, tissues and/or times, but not in other undesirable tissues. For example, increased resistance of a plant to infection by soil-borne pathogens might be accomplished by transforming the plant genome with a pathogen-resistance gene such that pathogen-resistance protein is robustly expressed within the roots of the plant. Alternatively, it may be desirable to express a transgene in plant tissues that are in a particular growth or developmental phase such as, for example, cell division or elongation. Another application is the desirability of using tissue specific promoters and/or 3' UTRs to confine the expression of the transgenes encoding an agronomic trait in specific tissues types like developing parenchyma cells. As such, a particular problem in the identification of promoters and/or 3' UTRs is how to identify the promoters, and to relate the identified promoter to developmental properties of the cell for specific tissue expression.

Another problem regarding the identification of a promoter is the requirement to clone all relevant cis-acting and trans-activating transcriptional control elements so that the cloned DNA fragment drives transcription in the wanted specific expression pattern. Given that such control elements are located distally from the translation initiation or start site, the size of the polynucleotide that is selected to comprise the promoter is of importance for providing the level of expression and the expression patterns of the promoter polynucleotide sequence. It is known that promoter lengths include functional information, and different genes have been shown to have promoters longer or shorter than promoters of the other genes in the genome. Elucidating the transcription start site of a promoter and predicting the functional gene elements in the promoter region is challenging. Further adding to the challenge are the complexity, diversity and inherent degenerate nature of regulatory motifs and cis- and trans-regulatory elements (Blanchette, Mathieu, et al. "Genome-wide computational prediction of transcriptional regulatory modules reveals new insights into human gene expression." *Genome research* 16.5 (2006): 656-668). The cis- and trans-regulatory elements are located in the distal parts of the promoter which regulate the spatial and temporal expression of a gene to occur only at required sites and at specific times (Porto, Milena Silva, et al. "Plant promoters: an approach of structure and function." *Molecular biotechnology* 56.1 (2014): 38-49). Existing promoter analysis tools cannot reliably identify such cis regulatory elements in a genomic sequence, thus predicting too many false positives because these tools are generally focused only on the sequence content (Fickett J W, Hatzigeorgiou A G (1997) Eukaryotic promoter recognition. Genome research 7: 861-878). Accordingly, the identification of promoter regulatory elements requires that an appropriate sequence of a specific size is obtained that will result in driving expression of an operably linked transgene in a desirable manner.

Provided are methods and compositions for overcoming such problems through the use of *Zea mays* KNOTTED1 (KN1) regulatory elements to express transgenes in planta.

II. Terms and Abbreviations

Throughout the application, a number of terms are used. In order to provide a clear and consistent understanding of the specification and claims, including the scope to be given such terms, the following definitions are provided.

As used herein, the term "intron" refers to any nucleic acid sequence comprised in a gene (or expressed polynucleotide sequence of interest) that is transcribed but not translated. Introns include untranslated nucleic acid sequence within an expressed sequence of DNA, as well as the corresponding sequence in RNA molecules transcribed therefrom. A construct described herein can also contain sequences that enhance translation and/or mRNA stability such as introns. An example of one such intron is the first intron of gene II of the histone H3 variant of *Arabidopsis thaliana* or any other commonly known intron sequence. Introns can be used in combination with a promoter sequence to enhance translation and/or mRNA stability.

The term "isolated", as used herein means having been removed from its natural environment, or removed from other compounds present when the compound is first formed. The term "isolated" embraces materials isolated from natural sources as well as materials (e.g., nucleic acids and proteins) recovered after preparation by recombinant expression in a host cell, or chemically-synthesized compounds such as nucleic acid molecules, proteins, and peptides.

The term "purified", as used herein relates to the isolation of a molecule or compound in a form that is substantially free of contaminants normally associated with the molecule or compound in a native or natural environment, or substantially enriched in concentration relative to other compounds present when the compound is first formed, and means having been increased in purity as a result of being separated from other components of the original composition. The term "purified nucleic acid" is used herein to describe a nucleic acid sequence which has been separated, produced apart from, or purified away from other biological compounds including, but not limited to polypeptides, lipids and carbohydrates, while effecting a chemical or functional change in the component (e.g., a nucleic acid may be purified from a chromosome by removing protein contaminants and breaking chemical bonds connecting the nucleic acid to the remaining DNA in the chromosome).

The term "synthetic", as used herein refers to a polynucleotide (i.e., a DNA or RNA) molecule that was created via chemical synthesis as an in vitro process. For example, a synthetic DNA may be created during a reaction within an Eppendorf™ tube, such that the synthetic DNA is enzymatically produced from a native strand of DNA or RNA. Other laboratory methods may be utilized to synthesize a polynucleotide sequence. Oligonucleotides may be chemically synthesized on an oligo synthesizer via solid-phase synthesis using phosphoramidites. The synthesized oligonucleotides may be annealed to one another as a complex, thereby producing a "synthetic" polynucleotide. Other methods for chemically synthesizing a polynucleotide are known in the art, and can be readily implemented for use in the present disclosure.

The term "about" as used herein means greater or lesser than the value or range of values stated by 10 percent, but is not intended to designate any value or range of values to only this broader definition. Each value or range of values preceded by the term "about" is also intended to encompass the embodiment of the stated absolute value or range of values.

For the purposes of the present disclosure, a "gene," includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites, introns and locus control regions.

As used herein the terms "native" or "natural" define a condition found in nature. A "native DNA sequence" is a DNA sequence present in nature that was produced by natural means or traditional breeding techniques but not generated by genetic engineering (e.g., using molecular biology/transformation techniques).

As used herein a "transgene" is defined to be a nucleic acid sequence that encodes a gene product, including for example, but not limited to, an mRNA. In one embodiment the transgene is an exogenous nucleic acid, where the transgene sequence has been introduced into a host cell by genetic engineering (or the progeny thereof) where the transgene is not normally found. In one example, a transgene encodes an industrially or pharmaceutically useful compound, or a gene encoding a desirable agricultural trait (e.g., an herbicide-resistance gene). In yet another example, a transgene is an antisense nucleic acid sequence, wherein expression of the antisense nucleic acid sequence inhibits expression of a target nucleic acid sequence. In one embodiment the transgene is an endogenous nucleic acid, wherein additional genomic copies of the endogenous nucleic acid are desired, or a nucleic acid that is in the antisense orientation with respect to the sequence of a target nucleic acid in a host organism.

As used herein the term "non-*Zea mays* KN1 transgene" or "non-ZmKN1 gene" is any transgene that has less than 80% sequence identity with the *Zea mays* KN1 gene coding sequence (SEQ ID NO:5 with the Genbank NCBI Accession No. AY312169.1).

A "gene product" as defined herein is any product produced by the gene. For example the gene product can be the direct transcriptional product of a gene (e.g., mRNA, tRNA, rRNA, antisense RNA, interfering RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation. Gene expression can be influenced by external signals, for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein the term "gene expression" relates to the process by which the coded information of a nucleic acid transcriptional unit (including, e.g., genomic DNA) is converted into an operational, non-operational, or structural part of a cell, often including the synthesis of a protein. Gene expression can be influenced by external signals; for example, exposure of a cell, tissue, or organism to an agent that increases or decreases gene expression. Expression of a gene can also be regulated anywhere in the pathway from DNA to RNA to protein. Regulation of gene expression occurs, for example, through controls acting on transcription, translation, RNA transport and processing, degradation of intermediary molecules such as mRNA, or through activation, inactivation, compartmentalization, or degradation of specific protein molecules after they have been made, or by combinations thereof. Gene expression can be measured at the RNA level or the protein level by any method known in the art, including, without limitation, Northern blot, RT-PCR, Western blot, or in vitro, in situ, or in vivo protein activity assay(s).

As used herein, "homology-based gene silencing" (HBGS) is a generic term that includes both transcriptional gene silencing and post-transcriptional gene silencing. Silencing of a target locus by an unlinked silencing locus can result from transcription inhibition (transcriptional gene silencing; TGS) or mRNA degradation (post-transcriptional gene silencing; PTGS), owing to the production of double-stranded RNA (dsRNA) corresponding to promoter or transcribed sequences, respectively. The involvement of distinct cellular components in each process suggests that dsRNA-induced TGS and PTGS likely result from the diversification of an ancient common mechanism. However, a strict comparison of TGS and PTGS has been difficult to achieve because it generally relies on the analysis of distinct silencing loci. In some instances, a single transgene locus can triggers both TGS and PTGS, owing to the production of dsRNA corresponding to promoter and transcribed sequences of different target genes. Mourrain et al. (2007) *Planta* 225:365-79. It is likely that siRNAs are the actual molecules that trigger TGS and PTGS on homologous sequences: the siRNAs would in this model trigger silencing and methylation of homologous sequences in cis and in trans through the spreading of methylation of transgene sequences into the endogenous promoter.

As used herein, the term "nucleic acid molecule" (or "nucleic acid" or "polynucleotide") may refer to a polymeric form of nucleotides, which may include both sense and anti-sense strands of RNA, cDNA, genomic DNA, and synthetic forms and mixed polymers of the above. A nucleotide may refer to a ribonucleotide, deoxyribonucleotide, or a modified form of either type of nucleotide. A "nucleic acid molecule" as used herein is synonymous with "nucleic acid" and "polynucleotide". A nucleic acid molecule is usually at least 10 bases in length, unless otherwise specified. The term may refer to a molecule of RNA or DNA of indeterminate length. The term includes single- and double-stranded forms of DNA. A nucleic acid molecule may include either or both naturally-occurring and modified nucleotides linked together by naturally occurring and/or non-naturally occurring nucleotide linkages.

Nucleic acid molecules may be modified chemically or biochemically, or may contain non-natural or derivatized nucleotide bases, as will be readily appreciated by those of skill in the art. Such modifications include, for example, labels, methylation, substitution of one or more of the naturally occurring nucleotides with an analog, internucleotide modifications (e.g., uncharged linkages: for example, methyl phosphonates, phosphotriesters, phosphoramidites, carbamates, etc.; charged linkages: for example, phosphorothioates, phosphorodithioates, etc.; pendent moieties: for example, peptides; intercalators: for example, acridine, psoralen, etc.; chelators; alkylators; and modified linkages: for example, alpha anomeric nucleic acids, etc.). The term "nucleic acid molecule" also includes any topological conformation, including single-stranded, double-stranded, partially duplexed, triplexed, hairpinned, circular, and padlocked conformations.

Transcription proceeds in a 5' to 3' manner along a DNA strand. This means that RNA is made by the sequential addition of ribonucleotide-5'-triphosphates to the 3' terminus of the growing chain (with a requisite elimination of the pyrophosphate). In either a linear or circular nucleic acid molecule, discrete elements (e.g., particular nucleotide sequences) may be referred to as being "upstream" or "5'" relative to a further element if they are bonded or would be bonded to the same nucleic acid in the 5' direction from that element. Similarly, discrete elements may be "downstream" or "3'" relative to a further element if they are or would be bonded to the same nucleic acid in the 3' direction from that element.

A base "position", as used herein, refers to the location of a given base or nucleotide residue within a designated nucleic acid. The designated nucleic acid may be defined by alignment (see below) with a reference nucleic acid.

Hybridization relates to the binding of two polynucleotide strands via Hydrogen bonds. Oligonucleotides and their analogs hybridize by hydrogen bonding, which includes Watson-Crick, Hoogsteen or reversed Hoogsteen hydrogen bonding, between complementary bases. Generally, nucleic acid molecules consist of nitrogenous bases that are either pyrimidines (cytosine (C), uracil (U), and thymine (T)) or purines (adenine (A) and guanine (G)). These nitrogenous bases form hydrogen bonds between a pyrimidine and a purine, and the bonding of the pyrimidine to the purine is referred to as "base pairing." More specifically, A will hydrogen bond to T or U, and G will bond to C. "Complementary" refers to the base pairing that occurs between two distinct nucleic acid sequences or two distinct regions of the same nucleic acid sequence.

"Specifically hybridizable" and "specifically complementary" are terms that indicate a sufficient degree of complementarity such that stable and specific binding occurs between the oligonucleotide and the DNA or RNA target. The oligonucleotide need not be 100% complementary to its target sequence to be specifically hybridizable. An oligonucleotide is specifically hybridizable when binding of the oligonucleotide to the target DNA or RNA molecule interferes with the normal function of the target DNA or RNA, and there is sufficient degree of complementarity to avoid non-specific binding of the oligonucleotide to non-target sequences under conditions where specific binding is desired, for example under physiological conditions in the case of in vivo assays or systems. Such binding is referred to as specific hybridization.

Hybridization conditions resulting in particular degrees of stringency will vary depending upon the nature of the chosen hybridization method and the composition and length of the hybridizing nucleic acid sequences. Generally, the temperature of hybridization and the ionic strength (especially the Na+ and/or Mg2+ concentration) of the hybridization buffer will contribute to the stringency of hybridization, though wash times also influence stringency. Calculations regarding hybridization conditions required for attaining particular degrees of stringency are discussed in Sambrook et al. (ed.), *Molecular Cloning: A Laboratory Manual,* 2nd ed., vol. 1-3, Cold Spring Harbor Laboratory Press, Cold Spring Harbor, N.Y., 1989, chs. 9 and 11.

As used herein, "stringent conditions" encompass conditions under which hybridization will only occur if there is less than 50% mismatch between the hybridization molecule and the DNA target. "Stringent conditions" include further particular levels of stringency. Thus, as used herein, "moderate stringency" conditions are those under which molecules with more than 50% sequence mismatch will not hybridize; conditions of "high stringency" are those under which sequences with more than 20% mismatch will not hybridize; and conditions of "very high stringency" are those under which sequences with more than 10% mismatch will not hybridize.

In particular embodiments, stringent conditions can include hybridization at 65° C., followed by washes at 65° C. with 0.1×SSC/0.1% SDS for 40 minutes.

The following are representative, non-limiting hybridization conditions:

Very High Stringency: Hybridization in 5×SSC buffer at 65° C. for 16 hours; wash twice in 2×SSC buffer at room temperature for 15 minutes each; and wash twice in 0.5×SSC buffer at 65° C. for 20 minutes each.

High Stringency: Hybridization in 5x-6×SSC buffer at 65-70° C. for 16-20 hours; wash twice in 2×SSC buffer at room temperature for 5-20 minutes each; and wash twice in 1×SSC buffer at 55-70° C. for 30 minutes each.

Moderate Stringency: Hybridization in 6×SSC buffer at room temperature to 55° C. for 16-20 hours; wash at least twice in 2x-3×SSC buffer at room temperature to 55° C. for 20-30 minutes each.

In particular embodiments, specifically hybridizable nucleic acid molecules can remain bound under very high stringency hybridization conditions. In these and further embodiments, specifically hybridizable nucleic acid molecules can remain bound under high stringency hybridization conditions. In these and further embodiments, specifically hybridizable nucleic acid molecules can remain bound under moderate stringency hybridization conditions.

Oligonucleotide: An oligonucleotide is a short nucleic acid polymer. Oligonucleotides may be formed by cleavage of longer nucleic acid segments, or by polymerizing individual nucleotide precursors. Automated synthesizers allow the synthesis of oligonucleotides up to several hundred base pairs in length. Because oligonucleotides may bind to a complementary nucleotide sequence, they may be used as probes for detecting DNA or RNA. Oligonucleotides composed of DNA (oligodeoxyribonucleotides) may be used in PCR, a technique for the amplification of small DNA sequences. In PCR, the oligonucleotide is typically referred to as a "primer", which allows a DNA polymerase to extend the oligonucleotide and replicate the complementary strand.

As used herein, the term "sequence identity" or "identity", as used herein in the context of two nucleic acid or polypeptide sequences, may refer to the residues in the two sequences that are the same when aligned for maximum correspondence over a specified comparison window.

As used herein, the term "percentage of sequence identity" may refer to the value determined by comparing two optimally aligned sequences (e.g., nucleic acid sequences, and amino acid sequences) over a comparison window, wherein the portion of the sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleotide or amino acid residue occurs in both sequences to yield the number of matched positions, dividing the number of matched positions by the total number of positions in the comparison window, and multiplying the result by 100 to yield the percentage of sequence identity.

Methods for aligning sequences for comparison are well-known in the art. Various programs and alignment algorithms are described in, for example: Smith and Waterman (1981) *Adv. Appl. Math.* 2:482; Needleman and Wunsch (1970) *J. Mol. Biol.* 48:443; Pearson and Lipman (1988) *Proc. Natl. Acad. Sci. U.S.A.* 85:2444; Higgins and Sharp (1988) *Gene* 73:237-44; Higgins and Sharp (1989) *CABIOS* 5:151-3; Corpet et al. (1988) *Nucleic Acids Res.* 16:10881-90; Huang et al. (1992) *Comp. Appl. Biosci.* 8:155-65; Pearson et al. (1994) *Methods Mol. Biol.* 24:307-31; Tatiana et al. (1999) *FEMS Microbiol. Lett.* 174:247-50. A detailed consideration of sequence alignment methods and homology calculations can be found in, e.g., Altschul et al. (1990) *J. Mol. Biol.* 215:403-10.

The National Center for Biotechnology Information (NCBI) Basic Local Alignment Search Tool (BLAST™; Altschul et al. (1990)) is available from several sources, including the National Center for Biotechnology Information (Bethesda, Md.), and on the internet, for use in connection with several sequence analysis programs. A description of how to determine sequence identity using this program is available on the internet under the "help" section for BLAST™. For comparisons of nucleic acid sequences, the "Blast 2 sequences" function of the BLAST™ (Blastn) program may be employed using the default parameters. Nucleic acid sequences with even greater similarity to the reference sequences will show increasing percentage identity when assessed by this method.

As used herein the term "operably linked" relates to a first nucleic acid sequence is operably linked with a second nucleic acid sequence when the first nucleic acid sequence is in a functional relationship with the second nucleic acid sequence. For instance, a promoter is operably linked with a coding sequence when the promoter affects the transcription or expression of the coding sequence. When recombinantly produced, operably linked nucleic acid sequences are generally contiguous and, where necessary to join two protein-coding regions, in the same reading frame. However, elements need not be contiguous to be operably linked.

As used herein, the term "promoter" refers to a region of DNA that generally is located upstream (towards the 5' region of a gene) of a gene and is needed to initiate and drive transcription of the gene. A promoter may permit proper activation or repression of a gene that it controls. A promoter may contain specific sequences that are recognized by transcription factors. These factors may bind to a promoter DNA sequence, which results in the recruitment of RNA polymerase, an enzyme that synthesizes RNA from the coding region of the gene. The promoter generally refers to all gene regulatory elements located upstream of the gene, including, upstream promoters, 5'-UTR, introns, and leader sequences.

As used herein, the term "upstream-promoter" refers to a contiguous polynucleotide sequence that is sufficient to direct initiation of transcription. As used herein, an upstream-promoter encompasses the site of initiation of transcription with several sequence motifs, which include TATA Box, initiator sequence, TFIIB recognition elements and other promoter motifs (Jennifer, E. F. et al., (2002) *Genes & Dev.,* 16: 2583-2592). The upstream promoter provides the site of action to RNA polymerase II which is a multi-subunit enzyme with the basal or general transcription factors like, TFIIA, B, D, E, F and H. These factors assemble into a transcription pre initiation complex that catalyzes the synthesis of RNA from DNA template.

The activation of the upstream-promoter is done by the additional sequence of regulatory DNA sequence elements to which various proteins bind and subsequently interact with the transcription initiation complex to activate gene expression. These gene regulatory elements sequences interact with specific DNA-binding factors. These sequence motifs may sometimes be referred to as cis-elements. Such cis-elements, to which tissue-specific or development-specific transcription factors bind, individually or in combination, may determine the spatiotemporal expression pattern of a promoter at the transcriptional level. These cis-elements vary widely in the type of control they exert on operably linked genes. Some elements act to increase the transcription of operably-linked genes in response to environmental responses (e.g., temperature, moisture, and wounding). Other cis-elements may respond to developmental cues (e.g., germination, seed maturation, and flowering) or to spatial information (e.g., tissue specificity). See, for example, Langridge et al., (1989) *Proc. Natl. Acad. Sci. USA* 86:3219-23. These cis-elements are located at a varying distance from transcription start point, some cis-elements (called proximal elements) are adjacent to a minimal core promoter region while other elements can be positioned several kilobases upstream or downstream of the promoter (enhancers).

As used herein, the terms "5' untranslated region" or "5'-UTR" is defined as the untranslated segment in the 5' terminus of pre-mRNAs or mature mRNAs. For example, on mature mRNAs, a 5'-UTR typically harbors on its 5' end a 7-methylguanosine cap and is involved in many processes such as splicing, polyadenylation, mRNA export towards the cytoplasm, identification of the 5' end of the mRNA by the translational machinery, and protection of the mRNAs against degradation.

As used herein, the terms "transcription terminator" is defined as the transcribed segment in the 3' terminus of pre-mRNAs or mature mRNAs. For example, longer stretches of DNA beyond "polyadenylation signal" site is transcribed as a pre-mRNA. This DNA sequence usually contains transcription termination signal for the proper processing of the pre-mRNA into mature mRNA.

As used herein, the term "3' untranslated region" or "3'-UTR" is defined as the untranslated segment in a 3' terminus of the pre-mRNAs or mature mRNAs. For example, on mature mRNAs this region harbors the poly-(A) tail and is known to have many roles in mRNA stability, translation initiation, and mRNA export. In addition, the 3'-UTR is considered to include the polyadenylation signal and transcription terminator.

As used herein, the term "polyadenylation signal" designates a nucleic acid sequence present in mRNA transcripts that allows for transcripts, when in the presence of a poly-(A) polymerase, to be polyadenylated on the polyadenylation site, for example, located 10 to 30 bases downstream of the poly-(A) signal. Many polyadenylation signals are known in the art and are useful for the present invention. An exemplary sequence includes AAUAAA and variants thereof, as described in Loke J., et al., (2005) *Plant Physiology* 138(3); 1457-1468.

A "DNA binding transgene" is a polynucleotide coding sequence that encodes a DNA binding protein. The DNA binding protein is subsequently able to bind to another molecule. A binding protein can bind to, for example, a DNA molecule (a DNA-binding protein), a RNA molecule (an RNA-binding protein), and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding, and protein-binding activity.

Examples of DNA binding proteins include; meganucleases, zinc fingers, CRISPRs, and TALEN binding domains that can be "engineered" to bind to a predetermined nucleotide sequence. Typically, the engineered DNA binding proteins (e.g., zinc fingers, CRISPRs, or TALENs) are proteins that are non-naturally occurring. Non-limiting examples of methods for engineering DNA-binding proteins are design and selection. A designed DNA binding protein is a protein not occurring in nature whose design/composition results principally from rational criteria. Rational criteria for design include application of substitution rules and computerized algorithms for processing information in a database storing information of existing ZFP, CRISPR, and/or TALEN designs and binding data. See, for example, U.S. Pat. Nos. 6,140,081; 6,453,242; and 6,534,261; see also WO 98/53058; WO 98/53059; WO 98/53060; WO 02/016536 and WO 03/016496 and U.S. Publication Nos. 20110301073, 20110239315 and 20119145940.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP. Zinc finger binding domains can be "engineered" to bind to a predetermined nucleotide sequence. Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261 and 6,794,136; see also WO 98/53058; WO 98/53059; WO 98/53060; WO 02/016536 and WO 03/016496.

In other examples, the DNA-binding domain of one or more of the nucleases comprises a naturally occurring or engineered (non-naturally occurring) TAL effector DNA binding domain. See, e.g., U.S. Patent Publication No. 20110301073, incorporated by reference in its entirety herein. The plant pathogenic bacteria of the genus Xanthomonas are known to cause many diseases in important crop plants. Pathogenicity of Xanthomonas depends on a conserved type III secretion (T3S) system which injects more than different effector proteins into the plant cell. Among these injected proteins are transcription activator-like (TALEN) effectors which mimic plant transcriptional activators and manipulate the plant transcriptome (see Kay et al., (2007) *Science* 318:648-651). These proteins contain a DNA binding domain and a transcriptional activation domain. One of the most well characterized TAL-effectors is AvrBs3 from *Xanthomonas campestgris* pv. *Vesicatoria* (see Bonas et al., (1989) *Mol Gen Genet* 218: 127-136 and WO2010079430). TAL-effectors contain a centralized domain of tandem repeats, each repeat containing approximately 34 amino acids, which are key to the DNA binding specificity of these proteins. In addition, they contain a nuclear localization sequence and an acidic transcriptional activation domain (for a review see Schornack S, et al., (2006) *J Plant Physiol* 163(3): 256-272). In addition, in the phytopathogenic bacteria *Ralstonia solanacearum* two genes, designated brg11 and hpx17 have been found that are homologous to the AvrBs3 family of *Xanthomonas* in the *R. solanacearum* biovar strain GMI1000 and in the biovar 4 strain RS1000 (See Heuer et al., (2007) *Appl and Enviro Micro* 73(13): 4379-4384). These genes are 98.9% identical in nucleotide sequence to each other but differ by a deletion of 1,575 bp in the repeat domain of hpx17. However, both gene products have less than 40% sequence identity with AvrBs3 family proteins of *Xanthomonas*. See, e.g., U.S. Patent Publication No. 20110301073, incorporated by reference in its entirety.

Specificity of these TAL effectors depends on the sequences found in the tandem repeats. The repeated sequence comprises approximately 102 bp and the repeats are typically 91-100% homologous with each other (Bonas et al., ibid). Polymorphism of the repeats is usually located at positions 12 and 13 and there appears to be a one-to-one correspondence between the identity of the hypervariable diresidues at positions 12 and 13 with the identity of the contiguous nucleotides in the TAL-effector's target sequence (see Moscou and Bogdanove, (2009) *Science* 326:1501 and Boch et al., (2009) *Science* 326:1509-1512). Experimentally, the natural code for DNA recognition of these TAL-effectors has been determined such that an HD sequence at positions 12 and 13 leads to a binding to cytosine (C), NG binds to T, NI to A, C, G or T, NN binds to A or G, and ING binds to T. These DNA binding repeats have been assembled into proteins with new combinations and numbers of repeats, to make artificial transcription factors that are able to interact with new sequences and activate the expression of a non-endogenous reporter gene in plant cells (Boch et al., ibid). Engineered TAL proteins have been linked to a FokI cleavage half domain to yield a TAL effector domain nuclease fusion (TALEN) exhibiting activity in a yeast reporter assay (plasmid based target).

The CRISPR (Clustered Regularly Interspaced Short Palindromic Repeats)/Cas (CRISPR Associated) nuclease system is a recently engineered nuclease system based on a bacterial system that can be used for genome engineering. It is based on part of the adaptive immune response of many bacteria and Archaea. When a virus or plasmid invades a bacterium, segments of the invader's DNA are converted into CRISPR RNAs (crRNA) by the 'immune' response. This crRNA then associates, through a region of partial complementarity, with another type of RNA called tracrRNA to guide the Cas9 nuclease to a region homologous to the crRNA in the target DNA called a "protospacer." Cas9 cleaves the DNA to generate blunt ends at the double-stranded break (DSB) at sites specified by a 20-nucleotide guide sequence contained within the crRNA transcript. Cas9 requires both the crRNA and the tracrRNA for site specific DNA recognition and cleavage. This system has now been engineered such that the crRNA and tracrRNA can be combined into one molecule (the "single guide RNA"), and the crRNA equivalent portion of the single guide RNA can be engineered to guide the Cas9 nuclease to target any desired sequence (see Jinek et al., (2012) Science 337, pp. 816-821, Jinek et al., (2013), eLife 2:e00471, and David Segal, (2013) eLife 2:e00563). Thus, the CRISPR/Cas system can be engineered to create a DSB at a desired target in a genome, and repair of the DSB can be influenced by the use of repair inhibitors to cause an increase in error prone repair.

In other examples, the DNA binding transgene is a site specific nuclease that comprises an engineered (non-naturally occurring) Meganuclease (also described as a homing endonuclease). The recognition sequences of homing endonucleases or meganucleases such as I-SceI, I-CeuI, PI-PspI, PI-Sce, I-SceIV, I-CsmI, I-PanI, I-SceII, I-PpoI, I-SceIII, I-CreI, I-TevI, I-TevII and I-TevIII are known. See also U.S.

Pat. No. 5,420,032; U.S. Pat. No. 6,833,252; Belfort et al., (1997) *Nucleic Acids Res.* 25:3379-30 3388; Dujon et al., (1989) *Gene* 82:115-118; Perler et al., (1994) *Nucleic Acids Res.* 22, 11127; Jasin (1996) *Trends Genet.* 12:224-228; Gimble et al., (1996) *J. Mol. Biol.* 263:163-180; Argast et al., (1998) *J. Mol. Biol.* 280:345-353 and the New England Biolabs catalogue. In addition, the DNA-binding specificity of homing endonucleases and meganucleases can be engineered to bind non-natural target sites. See, for example, Chevalier et al., (2002) *Molec. Cell* 10:895-905; Epinat et al., (2003) *Nucleic Acids Res.* 5 31:2952-2962; Ashworth et al., (2006) *Nature* 441:656-659; Paques et al., (2007) *Current Gene Therapy* 7:49-66; U.S. Patent Publication No. 20070117128. The DNA-binding domains of the homing endonucleases and meganucleases may be altered in the context of the nuclease as a whole (i.e., such that the nuclease includes the cognate cleavage domain) or may be fused to a heterologous cleavage domain.

As used herein, the term "transformation" encompasses all techniques that a nucleic acid molecule can be introduced into such a cell. Examples include, but are not limited to: transfection with viral vectors; transformation with plasmid vectors; electroporation; lipofection; microinjection (Mueller et al., (1978) Cell 15:579-85); *Agrobacterium*-mediated transfer; direct DNA uptake; WHISKERS™-mediated transformation; and microprojectile bombardment. These techniques may be used for both stable transformation and transient transformation of a plant cell. "Stable transformation" refers to the introduction of a nucleic acid fragment into a genome of a host organism resulting in genetically stable inheritance. Once stably transformed, the nucleic acid fragment is stably integrated in the genome of the host organism and any subsequent generation. Host organisms containing the transformed nucleic acid fragments are referred to as "transgenic" organisms. "Transient transformation" refers to the introduction of a nucleic acid fragment into the nucleus, or DNA-containing organelle, of a host organism resulting in gene expression without genetically stable inheritance.

An exogenous nucleic acid sequence. In one example, a transgene is a gene sequence (e.g., an herbicide-resistance gene), a gene encoding an industrially or pharmaceutically useful compound, or a gene encoding a desirable agricultural trait. In yet another example, the transgene is an antisense nucleic acid sequence, wherein expression of the antisense nucleic acid sequence inhibits expression of a target nucleic acid sequence. A transgene may contain regulatory sequences operably linked to the transgene (e.g., a promoter). In some embodiments, a polynucleotide sequence of interest is a transgene. However, in other embodiments, a polynucleotide sequence of interest is an endogenous nucleic acid sequence, wherein additional genomic copies of the endogenous nucleic acid sequence are desired, or a nucleic acid sequence that is in the antisense orientation with respect to the sequence of a target nucleic acid molecule in the host organism.

As used herein, the term a transgenic "event" is produced by transformation of plant cells with heterologous DNA, i.e., a nucleic acid construct that includes a transgene of interest, regeneration of a population of plants resulting from the insertion of the transgene into the genome of the plant, and selection of a particular plant characterized by insertion into a particular genome location. The term "event" refers to the original transformant and progeny of the transformant that include the heterologous DNA. The term "event" also refers to progeny produced by a sexual outcross between the transformant and another variety that includes the genomic/transgene DNA. Even after repeated back-crossing to a recurrent parent, the inserted transgene DNA and flanking genomic DNA (genomic/transgene DNA) from the transformed parent is present in the progeny of the cross at the same chromosomal location. The term "event" also refers to DNA from the original transformant and progeny thereof comprising the inserted DNA and flanking genomic sequence immediately adjacent to the inserted DNA that would be expected to be transferred to a progeny that receives inserted DNA including the transgene of interest as the result of a sexual cross of one parental line that includes the inserted DNA (e.g., the original transformant and progeny resulting from selfing) and a parental line that does not contain the inserted DNA.

As used herein, the terms "Polymerase Chain Reaction" or "PCR" define a procedure or technique in which minute amounts of nucleic acid, RNA and/or DNA, are amplified as described in U.S. Pat. No. 4,683,195 issued Jul. 28, 1987. Generally, sequence information from the ends of the region of interest or beyond needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage or plasmid sequences, etc. See generally Mullis et al., *Cold Spring Harbor Symp. Quant. Biol.*, 51:263 (1987); Erlich, ed., PCR Technology, (Stockton Press, N Y, 1989).

As used herein, the term "primer" refers to an oligonucleotide capable of acting as a point of initiation of synthesis along a complementary strand when conditions are suitable for synthesis of a primer extension product. The synthesizing conditions include the presence of four different deoxyribonucleotide triphosphates and at least one polymerization-inducing agent such as reverse transcriptase or DNA polymerase. These are present in a suitable buffer, which may include constituents which are co-factors or which affect conditions such as pH and the like at various suitable temperatures. A primer is preferably a single strand sequence, such that amplification efficiency is optimized, but double stranded sequences can be utilized.

As used herein, the term "probe" refers to an oligonucleotide that hybridizes to a target sequence. In the TaqMan® or TaqMae-style assay procedure, the probe hybridizes to a portion of the target situated between the annealing site of the two primers. A probe includes about eight nucleotides, about ten nucleotides, about fifteen nucleotides, about twenty nucleotides, about thirty nucleotides, about forty nucleotides, or about fifty nucleotides. In some embodiments, a probe includes from about eight nucleotides to about fifteen nucleotides. A probe can further include a detectable label, e.g., a fluorophore (Texas-Red®, Fluorescein isothiocyanate, etc.,). The detectable label can be covalently attached directly to the probe oligonucleotide, e.g., located at the probe's 5' end or at the probe's 3' end. A probe including a fluorophore may also further include a quencher, e.g., Black Hole Quencher™, Iowa Black™, etc.

As used herein, the terms "restriction endonucleases" and "restriction enzymes" refer to bacterial enzymes, each of which cut double-stranded DNA at or near a specific nucleotide sequence. Type-2 restriction enzymes recognize and cleave DNA at the same site, and include but are not limited to XbaI, BamHI, HindIII, EcoRI, XhoI, SalI, KpnI, AvaI, PstI and SmaI.

As used herein, the term "vector" is used interchangeably with the terms "construct", "cloning vector" and "expression vector" and means the vehicle by which a DNA or RNA sequence (e.g. a foreign gene) can be introduced into a host cell, so as to transform the host and promote expression (e.g. transcription and translation) of the introduced sequence. A "non-viral vector" is intended to mean any vector that does not comprise a virus or retrovirus. In some embodiments a "vector" is a sequence of DNA comprising at least one origin of DNA replication and at least one selectable marker gene. Examples include, but are not limited to, a plasmid, cosmid, bacteriophage, bacterial artificial chromosome (BAC), or virus that carries exogenous DNA into a cell. A vector can also include one or more genes, antisense molecules, and/or selectable marker genes and other genetic elements known in the art. A vector may transduce, transform, or infect a cell, thereby causing the cell to express the nucleic acid molecules and/or proteins encoded by the vector. The term "plasmid" defines a circular strand of nucleic acid capable of autosomal replication in either a prokaryotic or a eukaryotic host cell. The term includes nucleic acid which may be either DNA or RNA and may be single- or double-stranded. The plasmid of the definition may also include the sequences which correspond to a bacterial origin of replication.

As used herein, the term "selectable marker gene" as used herein defines a gene or other expression cassette which encodes a protein which facilitates identification of cells into which the selectable marker gene is inserted. For example a "selectable marker gene" encompasses reporter genes as well as genes used in plant transformation to, for example, protect plant cells from a selective agent or provide resistance/tolerance to a selective agent. In one embodiment only those cells or plants that receive a functional selectable marker are capable of dividing or growing under conditions having a selective agent. Examples of selective agents can include, for example, antibiotics, including spectinomycin, neomycin, kanamycin, paromomycin, gentamicin, and hygromycin. These selectable markers include neomycin phosphotransferase (npt II), which expresses an enzyme conferring resistance to the antibiotic kanamycin, and genes for the related antibiotics neomycin, paromomycin, gentamicin, and G418, or the gene for hygromycin phosphotransferase (hpt), which expresses an enzyme conferring resistance to hygromycin. Other selectable marker genes can include genes encoding herbicide resistance including bar or pat (resistance against glufosinate ammonium or phosphinothricin), acetolactate synthase (ALS, resistance against inhibitors such as sulfonylureas (SUs), imidazolinones (IMIs), triazolopyrimidines (TPs), pyrimidinyl oxybenzoates (POBs), and sulfonylamino carbonyl triazolinones that prevent the first step in the synthesis of the branched-chain amino acids), glyphosate, 2,4-D, and metal resistance or sensitivity. Examples of "reporter genes" that can be used as a selectable marker gene include the visual observation of expressed reporter gene proteins such as proteins encoding β-glucuronidase (GUS), luciferase, green fluorescent protein (GFP), yellow fluorescent protein (YFP), DsRed, β-galactosidase, chloramphenicol acetyltransferase (CAT), alkaline phosphatase, and the like. The phrase "marker-positive" refers to plants that have been transformed to include a selectable marker gene.

As used herein, the term "detectable marker" refers to a label capable of detection, such as, for example, a radioisotope, fluorescent compound, bioluminescent compound, a chemiluminescent compound, metal chelator, or enzyme. Examples of detectable markers include, but are not limited to, the following: fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In an embodiment, a detectable marker can be attached by spacer arms of various lengths to reduce potential steric hindrance.

As used herein, the terms "cassette", "expression cassette" and "gene expression cassette" refer to a segment of DNA that can be inserted into a nucleic acid or polynucleotide at specific restriction sites or by homologous recombination. As used herein the segment of DNA comprises a polynucleotide that encodes a polypeptide of interest, and the cassette and restriction sites are designed to ensure insertion of the cassette in the proper reading frame for transcription and translation. In an embodiment, an expression cassette can include a polynucleotide that encodes a polypeptide of interest and having elements in addition to the polynucleotide that facilitate transformation of a particular host cell. In an embodiment, a gene expression cassette may also include elements that allow for enhanced expression of a polynucleotide encoding a polypeptide of interest in a host cell. These elements may include, but are not limited to: a promoter, a minimal promoter, an enhancer, a response element, a terminator sequence, a polyadenylation sequence, and the like.

As used herein a "linker" or "spacer" is a bond, molecule or group of molecules that binds two separate entities to one another. Linkers and spacers may provide for optimal spacing of the two entities or may further supply a labile linkage that allows the two entities to be separated from each other. Labile linkages include photocleavable groups, acid-labile moieties, base-labile moieties and enzyme-cleavable groups. The terms "polylinker" or "multiple cloning site" as used herein defines a cluster of three or more Type-2 restriction enzyme sites located within 10 nucleotides of one another on a nucleic acid sequence. In other instances the term "polylinker" as used herein refers to a stretch of nucleotides that are targeted for joining two sequences via any known seamless cloning method (i.e., Gibson Assembly®, NEBuilder HiFiDNA Assembly®, Golden Gate Assembly, BioBrick® Assembly, etc.). Constructs comprising a polylinker are utilized for the insertion and/or excision of nucleic acid sequences such as the coding region of a gene.

As used herein, the term "control" refers to a sample used in an analytical procedure for comparison purposes. A control can be "positive" or "negative". For example, where the purpose of an analytical procedure is to detect a differentially expressed transcript or polypeptide in cells or tissue, it is generally preferable to include a positive control, such as a sample from a known plant exhibiting the desired expression, and a negative control, such as a sample from a known plant lacking the desired expression.

As used herein, the term "plant" includes a whole plant and any descendant, cell, tissue, or part of a plant. A class of plant that can be used in the present invention is generally as broad as the class of higher and lower plants amenable to mutagenesis including angiosperms (monocotyledonous and dicotyledonous plants), gymnosperms, ferns and multicellular algae. Thus, "plant" includes dicot and monocot plants. The term "plant parts" include any part(s) of a plant, including, for example and without limitation: seed (including mature seed and immature seed); a plant cutting; a plant cell; a plant cell culture; a plant organ (e.g., pollen, embryos, flowers, fruits, shoots, leaves, roots, stems, and explants). A plant tissue or plant organ may be a seed, protoplast, callus, or any other group of plant cells that is organized into a structural or functional unit. A plant cell or tissue culture may be capable of regenerating a plant having the physiological and morphological characteristics of the plant from which the cell or tissue was obtained, and of regenerating a plant having substantially the same genotype as the plant. In contrast, some plant cells are not capable of being regenerated to produce plants. Regenerable cells in a plant cell or tissue culture may be embryos, protoplasts, meristematic cells, callus, pollen, leaves, anthers, roots, root tips, silk, flowers, kernels, ears, cobs, husks, or stalks.

Plant parts include harvestable parts and parts useful for propagation of progeny plants. Plant parts useful for propagation include, for example and without limitation: seed; fruit; a cutting; a seedling; a tuber; and a rootstock. A harvestable part of a plant may be any useful part of a plant, including, for example and without limitation: flower; pollen; seedling; tuber; leaf; stem; fruit; seed; and root.

A plant cell is the structural and physiological unit of the plant, comprising a protoplast and a cell wall. A plant cell may be in the form of an isolated single cell, or an aggregate of cells (e.g., a friable callus and a cultured cell), and may be part of a higher organized unit (e.g., a plant tissue, plant organ, and plant). Thus, a plant cell may be a protoplast, a gamete producing cell, or a cell or collection of cells that can regenerate into a whole plant. As such, a seed, which comprises multiple plant cells and is capable of regenerating into a whole plant, is considered a "plant cell" in embodiments herein.

As used herein, the term "small RNA" refers to several classes of non-coding ribonucleic acid (ncRNA). The term small RNA describes the short chains of ncRNA produced in bacterial cells, animals, plants, and fungi. These short chains of ncRNA may be produced naturally within the cell or may be produced by the introduction of an exogenous sequence that expresses the short chain or ncRNA. The small RNA sequences do not directly code for a protein, and differ in function from other RNA in that small RNA sequences are only transcribed and not translated. The small RNA sequences are involved in other cellular functions, including gene expression and modification. Small RNA molecules are usually made up of about 20 to 30 nucleotides. The small RNA sequences may be derived from longer precursors. The precursors form structures that fold back on each other in self-complementary regions; they are then processed by the nuclease Dicer in animals or DCL1 in plants.

Many types of small RNA exist either naturally or produced artificially, including microRNAs (miRNAs), short interfering RNAs (siRNAs), antisense RNA, short hairpin RNA (shRNA), and small nucleolar RNAs (snoRNAs). Certain types of small RNA, such as microRNA and siRNA, are important in gene silencing and RNA interference (RNAi). Gene silencing is a process of genetic regulation in which a gene that would normally be expressed is "turned off" by an intracellular element, in this case, the small RNA. The protein that would normally be formed by this genetic information is not formed due to interference, and the information coded in the gene is blocked from expression.

As used herein, the term "small RNA" encompasses RNA molecules described in the literature as "tiny RNA" (Storz, (2002) Science 296:1260-3; Illangasekare et al., (1999) RNA 5:1482-1489); prokaryotic "small RNA" (sRNA) (Wassarman et al., (1999) Trends Microbiol. 7:37-45); eukaryotic "noncoding RNA (ncRNA)"; "micro-RNA (miRNA)"; "small non-mRNA (snmRNA)"; "functional RNA (fRNA)"; "transfer RNA (tRNA)"; "catalytic RNA" [e.g., ribozymes, including self-acylating ribozymes (Illangaskare et al., (1999) RNA 5:1482-1489); "small nucleolar RNAs (snoRNAs)," "tmRNA" (a.k.a. "10S RNA," Muto et al., (1998) Trends Biochem Sci. 23:25-29; and Gillet et al., (2001) Mol Microbiol. 42:879-885); RNAi molecules including without limitation "small interfering RNA (siRNA)," "endoribonuclease-prepared siRNA (e-siRNA)," "short hairpin RNA (shRNA)," and "small temporally regulated RNA (stRNA)," "diced siRNA (d-siRNA)," and aptamers, oligonucleotides and other synthetic nucleic acids that comprise at least one uracil base.

Unless otherwise specifically explained, all technical and scientific terms used herein have the same meaning as commonly understood by those of ordinary skill in the art to which this disclosure belongs. Definitions of common terms in molecular biology can be found in, for example: Lewin, Genes V, Oxford University Press, 1994 (ISBN 0-19-854287-9); Kendrew et al. (eds.), The Encyclopedia of Molecular Biology, Blackwell Science Ltd., 1994 (ISBN 0-632-02182-9); and Meyers (ed.), Molecular Biology and Biotechnology: A Comprehensive Desk Reference, VCH Publishers, Inc., 1995 (ISBN 1-56081-569-8).

As used herein, the articles, "a," "an," and "the" include plural references unless the context clearly and unambiguously dictates otherwise.

III. Zea mays KN1 Gene Regulatory Elements and Nucleic Acids Comprising the Same Provided are methods and compositions for using a promoter from a Zea mays KN1gene to express non-Zea mays KN1 transgenes in plant. In an embodiment, a promoter can be the Zea mays KN1gene promoter of SEQ ID NO:1.

In an embodiment, a polynucleotide is provided comprising a promoter, wherein the promoter is at least 80%, 85%, 90%, 91%, 92%, 93%, 94%, 95%, 96%, 97%, 98%, 99%, 99.5%, 99.8%, or 100% identical to SEQ ID NO:1. In an embodiment, a promoter is a Zea mays KN1gene promoter comprising a polynucleotide of at least 80%, 85%, 90%, 91%, 92%, 93%, 94%, 95%, 96%, 97%, 98%, 99%, 99.5%, 99.8%, or 100% identity to the polynucleotide of SEQ ID NO:1. In an embodiment, an isolated polynucleotide is provided comprising at least 80%, 85%, 90%, 91%, 92%, 93%, 94%, 95%, 96%, 97%, 98%, 99%, 99.5%, 99.8%, or 100% identity to the polynucleotide of SEQ ID NO:1. In an embodiment, a nucleic acid vector is provided comprising a Zea mays KN1gene promoter of SEQ ID NO:1. In an embodiment, a polynucleotide is provided comprising a Zea mays KN1gene promoter that is operably linked to a polylinker. In an embodiment, a gene expression cassette is provided comprising a Zea mays KN1gene promoter that is operably linked to a non metallothionein-like transgene. In an embodiment, a nucleic acid vector is provided comprising a Zea mays KN1gene promoter that is operably linked to a non Zea mays KN1 transgene. In one embodiment, the promoter consists of SEQ ID NO: 1. In an illustrative embodiment, a nucleic acid vector comprises a Zea mays KN1gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, selectable marker transgene, or combinations thereof.

In an embodiment, a nucleic acid vector comprises a gene expression cassette as disclosed herein. In an embodiment, a vector can be a plasmid, a cosmid, a bacterial artificial chromosome (BAC), a bacteriophage, a virus, or an excised polynucleotide fragment for use in direct transformation or gene targeting such as a donor DNA.

Transgene expression may also be regulated by a 5'-UTR region located downstream of the promoter sequence. Both a promoter and a 5'-UTR can regulate transgene expression. While a promoter is necessary to drive transcription, the presence of a 5'-UTR can increase expression levels resulting in mRNA transcript for translation and protein synthesis. A 5'-UTR gene region aids stable expression of a transgene. In a further embodiment an 5'-UTR is operably linked to a *Zea mays* KN1gene promoter.

Transgene expression may also be regulated by an intron region located downstream of the promoter sequence. Both a promoter and an intron can regulate transgene expression. While a promoter is necessary to drive transcription, the presence of an intron can increase expression levels resulting in mRNA transcript for translation and protein synthesis. An intron gene region aids stable expression of a transgene. In a further embodiment an intron is operably linked to a *Zea mays* KN1gene promoter.

In an embodiment, a nucleic acid vector is provided comprising a *Zea mays* KN1gene promoter as described herein and an intron, wherein the intron is at least 80%, 85%, 90%, 91%, 92%, 93%, 94%, 95%, 96%, 97%, 98%, 99%, 99.5%, 99.8%, or 100% identical to the polynucleotide of SEQ ID NO:7. In an embodiment, a nucleic acid vector is provided comprising a *Zea mays* KN1gene promoter as described herein and the intron wherein the *Zea mays* KN1gene promoter and intron are both operably linked to opposite ends of a polylinker. In an embodiment, a gene expression cassette is provided comprising a *Zea mays* KN1gene promoter as described herein and a intron, wherein the *Zea mays* KN1gene promoter and intron are both operably linked to opposite ends of a non *Zea mays* KN1 transgene. In one embodiment the intron, consists of SEQ ID NO:7. In an aspect of this embodiment the intron, consists of SEQ ID NO:7. In another aspect of this embodiment the promoter consists of SEQ ID NO: 1. In an illustrative embodiment, a gene expression cassette comprises a *Zea mays* KN1 gene promoter and *Zea mays* alcohol dehydrogenase I intron 6/Maize Streak Virus leader 1 of SEQ ID NO:2 that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a small RNA transgene, a selectable marker transgene, or combinations thereof. In a further embodiment the transgene is operably linked to a *Zea mays* KN1gene promoter and an intron from any art recognize intron sequence.

In accordance with one embodiment a nucleic acid vector is provided comprising a recombinant gene expression cassette wherein the recombinant gene expression cassette comprises a *Zea mays* KN1gene promoter operably linked to a polylinker sequence, a non-*Zea mays* KN1gene or *Zea mays* KN1 transgene or combination thereof. In one embodiment the recombinant gene cassette comprises a *Zea mays* KN1gene promoter operably linked to a non-*Zea mays* KN1gene or transgene. In one embodiment the recombinant gene cassette comprises a *Zea mays* KN1gene promoter as disclosed herein is operably linked to a polylinker sequence. The polylinker is operably linked to the *Zea mays* KN1gene promoter in a manner such that insertion of a coding sequence into one of the restriction sites of the polylinker will operably link the coding sequence allowing for expression of the coding sequence when the vector is transformed or transfected into a host cell.

In accordance with one embodiment a nucleic acid vector is provided comprising a gene cassette that consists of a *Zea mays* KN1gene promoter and a non-*Zea mays* KN1gene. In an embodiment, the *Zea mays* KN1gene promoter of SEQ ID NO: 1 is operably linked to the 3' end of the non-*Zea mays* KN1gene or transgene. In a further embodiment the *Zea mays* KN1gene promoter sequence comprises SEQ ID NO: 1 or a sequence that has 80, 85, 90, 95, 99 or 100% sequence identity with SEQ ID NO: 1. In accordance with one embodiment a nucleic acid vector is provided comprising a gene cassette that consists of a *Zea mays* KN1gene promoter, a non-*Zea mays* KN1gene, wherein the *Zea mays* KN1gene promoter is operably linked to the 5' end of the non-*Zea mays* KN1gene, and the *Zea mays* KN1gene promoter sequence comprises SEQ ID NO:1 or a sequence that has 80, 85, 90, 95, 99 or 100% sequence identity with SEQ ID NO: 1. In a further embodiment the *Zea mays* KN1gene promoter sequence consists of SEQ ID NO: 1,or a 1,407 bp sequence that has 80, 85, 90, 95, or 99% sequence identity with SEQ ID NO: 1.

A *Zea mays* KN1gene promoter may also comprise one or more additional sequence elements. In some embodiments, a *Zea mays* KN1gene promoter may comprise an exon (e.g., a leader or signal peptide such as a chloroplast transit peptide or ER retention signal). For example and without limitation, a *Zea mays* KN1gene promoter may enco de an exon incorporated into the *Zea mays* KN1gene promoter as a further embodiment.

In one embodiment a nucleic acid construct is provided comprising a *Zea mays* KN1gene promoter and a non-*Zea mays* KN1gene and optionally one or more of the following elements:

a) a 5' untranslated region;

b) an intron; and c) a 3' untranslated region, wherein, the *Zea mays* KN1gene promoter consists of SEQ ID NO:1 or a sequence having 98% sequence identity with SEQ ID NO:1;

the intron region consists of a known intron sequence or an intron of SEQ ID NO:7; and the 3' untranslated region consists of a known 3' untranslated region; further wherein said *Zea mays* KN1gene promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In one embodiment a nucleic acid construct is provided comprising a *Zea mays* KN1gene promoter fused with a *Zea mays* alcohol dehydrogenase I intron 6 and a non-*Zea mays* transgene and optionally one or more of the following elements:

a) a 5' untranslated region; and b) a 3' untranslated region, wherein, the promoter and intron fusion consists of SEQ ID NO:2 or a sequence having 98% sequence identity with SEQ ID NO:2;

the 5' UTR region consists of a known 5' UTR sequence;

the 3' untranslated region consists of a known 3'UTR sequence; further wherein said *Zea mays* KN1gene promoter is operably linked to said transgene and each optional element, when present, is also operably linked to both the promoter and the transgene. In a further embodiment a transgenic cell is provided comprising the nucleic acid construct disclosed immediately above. In one embodiment the transgenic cell is a plant cell, and in a further embodiment a plant is provided wherein the plant comprises said transgenic cells.

In accordance with one embodiment the nucleic acid vector further comprises a sequence encoding a selectable maker. In accordance with one embodiment the recombinant gene cassette is operably linked to an *Agrobacterium* T-DNA border. In accordance with one embodiment the recombinant gene cassette further comprises a first and second T-DNA border, wherein the first T-DNA border is operably linked to one end of the gene construct, and the second T-DNA border is operably linked to the other end of the gene construct. The first and second *Agrobacterium* T-DNA borders can be independently selected from T-DNA border sequences originating from bacterial strains selected from the group consisting of a nopaline synthesizing *Agrobacterium* T-DNA border, an ocotopine synthesizing *Agrobacterium* T-DNA border, a mannopine synthesizing *Agrobacterium* T-DNA border, a succinamopine synthesizing *Agrobacterium* T-DNA border, or any combination thereof. In one embodiment an *Agrobacterium* strain selected from the group consisting of a nopaline synthesizing strain, a mannopine synthesizing strain, a succinamopine synthesizing strain, or an octopine synthesizing strain is provided, wherein said strain comprises a plasmid wherein the plasmid comprises a transgene operably linked to a sequence selected from SEQ ID NO:1 or a sequence having 80, 85, 90, 95, or 99% sequence identity with SEQ ID NO:1.

Transgenes of interest that are suitable for use in the present disclosed constructs include, but are not limited to, coding sequences that confer (1) resistance to pests or disease, (2) tolerance to herbicides, (3) value added agronomic traits, such as; yield improvement, nitrogen use efficiency, water use efficiency, and nutritional quality, (4) binding of a protein to DNA in a site specific manner, (5) expression of small RNA, and (6) selectable markers. In accordance with one embodiment, the transgene encodes a selectable marker or a gene product conferring insecticidal resistance, herbicide tolerance, small RNA expression, nitrogen use efficiency, water use efficiency, or nutritional quality.

1. Insect Resistance

Various selectable markers also described as reporter genes can be operably linked to the *Zea mays* KN1gene promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary insect resistance coding sequences are known in the art. As embodiments of insect resistance coding sequences that can be operably linked to the regulatory elements of the subject disclosure, the following traits are provided. Coding sequences that provide exemplary Lepidopteran insect resistance include: cry1A; cry1A.105; cry1Ab; cry1Ab(truncated); cry1Ab-Ac (fusion protein); cry1Ac (marketed as Widestrike®); cry1C; cry1F (marketed as Widestrike®); cry1Fa2; cry2Ab2; cry2Ae; cry9C; mocry1F; pinII (protease inhibitor protein); vip3A(a); and vip3Aa20. Coding sequences that provide exemplary Coleopteran insect resistance include: cry34Ab1 (marketed as Herculex®); cry35Ab1 (marketed as Herculex®); cry3A; cry3Bb1; dvsnf7; and mcry3A. Coding sequences that provide exemplary multi-insect resistance include ecry31.Ab. The above list of insect resistance genes is not meant to be limiting. Any insect resistance genes are encompassed by the present disclosure.

2. Herbicide Tolerance

Various selectable markers also described as reporter genes can be operably linked to the *Zea mays* KN1gene promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary herbicide tolerance coding sequences are known in the art. As embodiments of herbicide tolerance coding sequences that can be operably linked to the regulatory elements of the subject disclosure, the following traits are provided. The glyphosate herbicide contains a mode of action by inhibiting the EPSPS enzyme (5-enolpyruvylshikimate-3-phosphate synthase). This enzyme is involved in the biosynthesis of aromatic amino acids that are essential for growth and development of plants. Various enzymatic mechanisms are known in the art that can be utilized to inhibit this enzyme. The genes that encode such enzymes can be operably linked to the gene regulatory elements of the subject disclosure. In an embodiment, selectable marker genes include, but are not limited to genes encoding glyphosate resistance genes include: mutant EPSPS genes such as 2mEPSPS genes, cp4 EPSPS genes, mEPSPS genes, dgt-28 genes; aroA genes; and glyphosate degradation genes such as glyphosate acetyl transferase genes (gat) and glyphosate oxidase genes (gox). These traits are currently marketed as Gly-Tol™, Optimum® GAT®, Agrisure® GT and Roundup Ready®. Resistance genes for glufosinate and/or bialaphos compounds include dsm-2, bar and pat genes. The bar and pat traits are currently marketed as LibertyLink®. Also included are tolerance genes that provide resistance to 2,4-D such as aad-1 genes (it should be noted that aad-1 genes have further activity on arloxyphenoxypropionate herbicides) and aad-12 genes (it should be noted that aad-12 genes have further activity on pyidyloxyacetate synthetic auxins). These traits are marketed as Enlist® crop protection technology. Resistance genes for ALS inhibitors (sulfonylureas, imidazolinones, triazolopyrimidines, pyrimidinylthiobenzoates, and sulfonylamino-carbonyl-triazolinones) are known in the art. These resistance genes most commonly result from point mutations to the ALS encoding gene sequence. Other ALS inhibitor resistance genes include hra genes, the csr1-2 genes, Sr-HrA genes, and surB genes. Some of the traits are marketed under the tradename Clearfield®. Herbicides that inhibit HPPD include the pyrazolones such as pyrazoxyfen, benzofenap, and topramezone; triketones such as mesotrione, sulcotrione, tembotrione, benzobicyclon; and diketonitriles such as isoxaflutole. These exemplary HPPD herbicides can be tolerated by known traits. Examples of HPPD inhibitors include hppdPF_W336 genes (for resistance to isoxaflutole) and avhppd-03 genes (for resistance to meostrione). An example of oxynil herbicide tolerant traits include the bxn gene, which has been showed to impart resistance to the herbicide/antibiotic bromoxynil. Resistance genes for dicamba include the dicamba monooxygenase gene (dmo) as disclosed in International PCT Publication No. WO 2008/105890. Resistance genes for PPO or PROTOX inhibitor type herbicides (e.g., acifluorfen, butafenacil, flupropazil, pentoxazone, carfentrazone, fluazolate, pyraflufen, aclonifen, azafenidin, flumioxazin, flumiclorac, bifenox, oxyfluorfen, lactofen, fomesafen, fluoroglycofen, and sulfentrazone) are known in the art. Exemplary genes conferring resistance to PPO include over expression of a wild-type *Arabidopsis thaliana* PPO enzyme (Lermontova I and Grimm B, (2000) Overexpression of plastidic protoporphyrinogen IX oxidase leads to resistance to the diphenylether herbicide acifluorfen. *Plant Physiol* 122:75-83.), the *B. subtilis* PPO gene (Li, X. and Nicholl D. 2005. Development of PPO inhibitor-resistant cultures and crops. Pest Manag. Sci. 61:277-285 and Choi K W, Han O, Lee H J, Yun Y C, Moon Y H, Kim M K, Kuk Y I, Han S U and Guh J O, (1998) Generation of resistance to the diphenyl ether herbicide, oxyfluorfen, via expression of the *Bacillus subtilis* protoporphyrinogen oxidase gene in transgenic tobacco plants. *Biosci Biotechnol Biochem* 62:558-560.) Resistance genes for pyridinoxy or phenoxy proprionic acids and cyclohexones include the ACCase inhibitor-encoding genes (e.g., Accl-S1, Accl-S2 and Accl-S3). Exemplary genes conferring resistance to cyclohexanediones and/or aryloxyphenoxypropanoic acid include haloxyfop, diclofop, fenoxyprop, fluazifop, and quizalofop. Finally, herbicides can inhibit photosynthesis, including triazine or benzonitrile are provided tolerance by psbA genes (tolerance to triazine), 1s+ genes (tolerance to triazine), and nitrilase genes (tolerance to benzonitrile). The above list of herbicide tolerance genes is not meant to be limiting. Any herbicide tolerance genes are encompassed by the present disclosure.

3. Agronomic Traits

Various selectable markers also described as reporter genes can be operably linked to the *Zea mays* KN1gene promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary agronomic trait coding sequences are known in the art. As embodiments of agronomic trait coding sequences that can be operably linked to the regulatory elements of the subject disclosure, the following traits are provided. Delayed fruit softening as provided by the pg genes inhibit the production of polygalacturonase enzyme responsible for the breakdown of pectin molecules in the cell wall, and thus causes delayed softening of the fruit. Further, delayed fruit ripening/senescence of acc genes act to suppress the normal expression of the native acc synthase gene, resulting in reduced ethylene production and delayed fruit ripening. Whereas, the accd genes metabolize the precursor of the fruit ripening hormone ethylene, resulting in delayed fruit ripening. Alternatively, the sam-k genes cause delayed ripening by reducing S-adenosylmethionine (SAM), a substrate for ethylene production. Drought stress tolerance phenotypes as provided by cspB genes maintain normal cellular functions under water stress conditions by preserving RNA stability and translation. Another example includes the EcBetA genes that catalyze the production of the osmoprotectant compound glycine betaine conferring tolerance to water stress. In addition, the RmBetA genes catalyze the production of the osmoprotectant compound glycine betaine conferring tolerance to water stress. Photosynthesis and yield enhancement is provided with the bbx32 gene that expresses a protein that interacts with one or more endogenous transcription factors to regulate the plant's day/night physiological processes. Ethanol production can be increase by expression of the amy797E genes that encode a thermostable alpha-amylase enzyme that enhances bioethanol production by increasing the thermostability of amylase used in degrading starch. Finally, modified amino acid compositions can result by the expression of the cordapA genes that encode a dihydrodipicolinate synthase enzyme that increases the production of amino acid lysine. The above list of agronomic trait coding sequences is not meant to be limiting. Any agronomic trait coding sequence is encompassed by the present disclosure.

4. DNA Binding Proteins

Various selectable markers also described as reporter genes can be operably linked to the *Zea mays* KN1gene promoter comprising SEQ ID NO: 1, or a sequence that has 80, 85, 90, 95 or 99% sequence identity with SEQ ID NO: 1. The operably linked sequences can then be incorporated into a chosen vector to allow for identification and selectable of transformed plants ("transformants"). Exemplary DNA binding protein coding sequences are known in the art. As embodiments of DNA binding protein coding sequences that can be operably linked to the regulatory elements of the subject disclosure, the following types of DNA binding proteins can include; Zinc Fingers, TALENS, CRISPRS, and meganucleases. The above list of DNA binding protein coding sequences is not meant to be limiting. Any DNA binding protein coding sequences is encompassed by the present disclosure.

5. Small RNA

Various selectable markers also described as reporter genes can be operably linked to the *Zea mays* KN1gene promoter comprising SEQ ID NO: 1, or a sequence that has 80, 85, 90, 95 or 99% sequence identity with SEQ ID NO: 1. The operably linked sequences can then be incorporated into a chosen vector to allow for identification and selection of transformed plants ("transformants"). Exemplary small RNA traits are known in the art. As embodiments of small RNA coding sequences that can be operably linked to the regulatory elements of the subject disclosure, the following traits are provided. For example, delayed fruit ripening/senescence of the anti-efe small RNA delays ripening by suppressing the production of ethylene via silencing of the ACO gene that encodes an ethylene-forming enzyme. The altered lignin production of ccomt small RNA reduces content of guanacyl (G) lignin by inhibition of the endogenous S-adenosyl-L-methionine: trans-caffeoyl CoA 3-O-methyltransferase (CCOMT gene). Further, the Black Spot Bruise Tolerance in *Solanum verrucosum* can be reduced by the Ppo5 small RNA which triggers the degradation of Ppo5 transcripts to block black spot bruise development. Also included is the dvsnf7 small RNA that inhibits Western Corn Rootworm with dsRNA containing a 240 bp fragment of the Western Corn Rootworm Snf7 gene. Modified starch/carbohydrates can result from small RNA such as the pPhL small RNA (degrades PhL transcripts to limit the formation of reducing sugars through starch degradation) and pR1 small RNA (degrades R1 transcripts to limit the formation of reducing sugars through starch degradation). Additional, benefits such as reduced acrylamide resulting from the asn1 small RNA that triggers degradation of Asn1 to impair asparagine formation and reduce polyacrylamide. Finally, the non-browning phenotype of pgas ppo suppression small RNA results in suppressing PPO to produce apples with a non-browning phenotype. The above list of small RNAs is not meant to be limiting. Any small RNA encoding sequences are encompassed by the present disclosure.

6. Selectable Markers

Various selectable markers also described as reporter genes can be operably linked to the *Zea mays* KN1gene promoter comprising SEQ ID NO: 1, or a sequence that has 80, 85, 90, 95 or 99% sequence identity with SEQ ID NO: 1. The operably linked sequences can then be incorporated into a chosen vector to allow for identification and selectable of transformed plants ("transformants"). Many methods are available to confirm expression of selectable markers in transformed plants, including for example DNA sequencing and PCR (polymerase chain reaction), Southern blotting, RNA blotting, immunological methods for detection of a protein expressed from the vector. But, usually the reporter genes are observed through visual observation of proteins that when expressed produce a colored product. Exemplary reporter genes are known in the art and encode β-glucuronidase (GUS), luciferase, green fluorescent protein (GFP), yellow fluorescent protein (YFP, Phi-YFP), red fluorescent protein (DsRFP, RFP, etc), β-galactosidase, and the like (See Sambrook, et al., Molecular Cloning: A Laboratory Manual, Third Edition, Cold Spring Harbor Press, N.Y., 2001, the content of which is incorporated herein by reference in its entirety).

Selectable marker genes are utilized for selection of transformed cells or tissues. Selectable marker genes include genes encoding antibiotic resistance, such as those encoding neomycin phosphotransferase II (NEO), spectinomycin/streptinomycin resistance (AAD), and hygromycin phosphotransferase (HPT or HGR) as well as genes conferring resistance to herbicidal compounds. Herbicide resistance genes generally code for a modified target protein insensitive to the herbicide or for an enzyme that degrades or detoxifies the herbicide in the plant before it can act. For example, resistance to glyphosate has been obtained by using genes coding for mutant target enzymes, 5-enolpyruvylshikimate-3-phosphate synthase (EPSPS). Genes and mutants for EPSPS are well known, and further described below. Resistance to glufosinate ammonium, bromoxynil, and 2,4-dichlorophenoxyacetate (2,4-D) have been obtained by using bacterial genes encoding PAT or DSM-2, a nitrilase, an AAD-1, or an AAD-12, each of which are examples of proteins that detoxify their respective herbicides.

In an embodiment, herbicides can inhibit the growing point or meristem, including imidazolinone or sulfonylurea, and genes for resistance/tolerance of acetohydroxyacid synthase (AHAS) and acetolactate synthase (ALS) for these herbicides are well known. Glyphosate resistance genes include mutant 5-enolpyruvylshikimate-3-phosphate synthase (EPSPs) and dgt-28 genes (via the introduction of recombinant nucleic acids and/or various forms of in vivo mutagenesis of native EPSPs genes), aroA genes and glyphosate acetyl transferase (GAT) genes, respectively). Resistance genes for other phosphono compounds include bar and pat genes from *Streptomyces* species, including *Streptomyces hygroscopicus* and *Streptomyces viridichromogenes*, and pyridinoxy or phenoxy proprionic acids and cyclohexones (ACCase inhibitor-encoding genes). Exemplary genes conferring resistance to cyclohexanediones and/or aryloxyphenoxypropanoic acid (including haloxyfop, diclofop, fenoxyprop, fluazifop, quizalofop) include genes of acetyl coenzyme A carboxylase (ACCase); Accl-S1, Accl-S2 and Accl-S3. In an embodiment, herbicides can inhibit photosynthesis, including triazine (psbA and 1s+ genes) or benzonitrile (nitrilase gene). Furthermore, such selectable markers can include positive selection markers such as phosphomannose isomerase (PMI) enzyme.

In an embodiment, selectable marker genes include, but are not limited to genes encoding: 2,4-D; neomycin phosphotransferase II; cyanamide hydratase; aspartate kinase; dihydrodipicolinate synthase; tryptophan decarboxylase; dihydrodipicolinate synthase and desensitized aspartate kinase; bar gene; tryptophan decarboxylase; neomycin phosphotransferase (NEO); hygromycin phosphotransferase (HPT or HYG); dihydrofolate reductase (DHFR); phosphinothricin acetyltransferase; 2,2-dichloropropionic acid dehalogenase; acetohydroxyacid synthase; 5-enolpyruvyl-shikimate-phosphate synthase (aroA); haloarylnitrilase; acetyl-coenzyme A carboxylase; dihydropteroate synthase (sul I); and 32 kD photosystem II polypeptide (psbA). An embodiment also includes selectable marker genes encoding resistance to: chloramphenicol; methotrexate; hygromycin; spectinomycin; bromoxynil; glyphosate; and phosphinothricin. The above list of selectable marker genes is not meant to be limiting. Any reporter or selectable marker gene are encompassed by the present disclosure.

In some embodiments the coding sequences are synthesized for optimal expression in a plant. For example, in an embodiment, a coding sequence of a gene has been modified by codon optimization to enhance expression in plants. An insecticidal resistance transgene, an herbicide tolerance transgene, a nitrogen use efficiency transgene, a water use efficiency transgene, a nutritional quality transgene, a DNA binding transgene, or a selectable marker transgene can be optimized for expression in a particular plant species or alternatively can be modified for optimal expression in dicotyledonous or monocotyledonous plants. Plant preferred codons may be determined from the codons of highest frequency in the proteins expressed in the largest amount in the particular plant species of interest. In an embodiment, a coding sequence, gene, or transgene is designed to be expressed in plants at a higher level resulting in higher transformation efficiency. Methods for plant optimization of genes are well known. Guidance regarding the optimization and production of synthetic DNA sequences can be found in, for example, WO2013016546, WO2011146524, WO1997013402, U.S. Pat. No. 6,166,302, and U.S. Pat. No. 5,380,831, herein incorporated by reference.

Transformation

Suitable methods for transformation of plants include any method by which DNA can be introduced into a cell, for example and without limitation: electroporation (see, e.g., U.S. Pat. No. 5,384,253); micro-projectile bombardment (see, e.g., U.S. Pat. Nos. 5,015,580, 5,550,318, 5,538,880, 6,160,208, 6,399,861, and 6,403,865); *Agrobacterium*-mediated transformation (see, e.g., U.S. Pat. Nos. 5,635,055, 5,824,877, 5,591,616; 5,981,840, and 6,384,301); and protoplast transformation (see, e.g., U.S. Pat. No. 5,508,184).

A DNA construct may be introduced directly into the genomic DNA of the plant cell using techniques such as agitation with silicon carbide fibers (see, e.g., U.S. Pat. Nos. 5,302,523 and 5,464,765), or the DNA constructs can be introduced directly to plant tissue using biolistic methods, such as DNA particle bombardment (see, e.g., Klein et al. (1987) Nature 327:70-73). Alternatively, the DNA construct can be introduced into the plant cell via nanoparticle transformation (see, e.g., US Patent Publication No. 20090104700, which is incorporated herein by reference in its entirety).

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) Trends Plant Sci. 11(1):1-4.

Through the application of transformation techniques, cells of virtually any plant species may be stably transformed, and these cells may be developed into transgenic plants by well-known techniques. For example, techniques that may be particularly useful in the context of cotton transformation are described in U.S. Pat. Nos. 5,846,797, 5,159,135, 5,004,863, and 6,624,344; techniques for transforming *Brassica* plants in particular are described, for example, in U.S. Pat. No. 5,750,871; techniques for transforming soy bean are described, for example, in U.S. Pat. No. 6,384,301; and techniques for transforming *Zea mays* are described, for example, in U.S. Pat. Nos. 7,060,876 and 5,591,616, and International PCT Publication WO 95/06722.

After effecting delivery of an exogenous nucleic acid to a recipient cell, a transformed cell is generally identified for further culturing and plant regeneration. In order to improve the ability to identify transformants, one may desire to employ a selectable marker gene with the transformation vector used to generate the transformant. In an illustrative embodiment, a transformed cell population can be assayed by exposing the cells to a selective agent or agents, or the cells can be screened for the desired marker gene trait.

Cells that survive exposure to a selective agent, or cells that have been scored positive in a screening assay, may be cultured in media that supports regeneration of plants. In an embodiment, any suitable plant tissue culture media may be modified by including further substances, such as growth regulators. Tissue may be maintained on a basic media with growth regulators until sufficient tissue is available to begin plant regeneration efforts, or following repeated rounds of manual selection, until the morphology of the tissue is suitable for regeneration (e.g., at least 2 weeks), then transferred to media conducive to shoot formation. Cultures are transferred periodically until sufficient shoot formation has occurred. Once shoots are formed, they are transferred to media conducive to root formation. Once sufficient roots are formed, plants can be transferred to soil for further growth and maturity.

Molecular Confirmation

A transformed plant cell, callus, tissue or plant may be identified and isolated by selecting or screening the engineered plant material for traits encoded by the marker genes present on the transforming DNA. For instance, selection can be performed by growing the engineered plant material on media containing an inhibitory amount of the antibiotic or herbicide to which the transforming gene construct confers resistance. Further, transformed plants and plant cells can also be identified by screening for the activities of any visible marker genes (e.g., the β-glucuronidase, luciferase, or green fluorescent protein genes) that may be present on the recombinant nucleic acid constructs. Such selection and screening methodologies are well known to those skilled in the art. Molecular confirmation methods that can be used to identify transgenic plants are known to those with skill in the art. Several exemplary methods are further described below.

Molecular Beacons have been described for use in sequence detection. Briefly, a FRET oligonucleotide probe is designed that overlaps the flanking genomic and insert DNA junction. The unique structure of the FRET probe results in it containing a secondary structure that keeps the fluorescent and quenching moieties in close proximity. The FRET probe and PCR primers (one primer in the insert DNA sequence and one in the flanking genomic sequence) are cycled in the presence of a thermostable polymerase and dNTPs. Following successful PCR amplification, hybridization of the FRET probe(s) to the target sequence results in the removal of the probe secondary structure and spatial separation of the fluorescent and quenching moieties. A fluorescent signal indicates the presence of the flanking genomic/transgene insert sequence due to successful amplification and hybridization. Such a molecular beacon assay for detection of as an amplification reaction is an embodiment of the subject disclosure.

Hydrolysis probe assay, otherwise known as TAQMAN® (Life Technologies, Foster City, Calif.), is a method of detecting and quantifying the presence of a DNA sequence. Briefly, a FRET oligonucleotide probe is designed with one oligo within the transgene and one in the flanking genomic sequence for event-specific detection. The FRET probe and PCR primers (one primer in the insert DNA sequence and one in the flanking genomic sequence) are cycled in the presence of a thermostable polymerase and dNTPs. Hybridization of the FRET probe results in cleavage and release of the fluorescent moiety away from the quenching moiety on the FRET probe. A fluorescent signal indicates the presence of the flanking/transgene insert sequence due to successful amplification and hybridization. Such a hydrolysis probe assay for detection of as an amplification reaction is an embodiment of the subject disclosure.

KASPar® assays are a method of detecting and quantifying the presence of a DNA sequence. Briefly, the genomic DNA sample comprising the integrated gene expression cassette polynucleotide is screened using a polymerase chain reaction (PCR) based assay known as a KASPar® assay system. The KASPar® assay used in the practice of the subject disclosure can utilize a KASPar® PCR assay mixture which contains multiple primers. The primers used in the PCR assay mixture can comprise at least one forward primers and at least one reverse primer. The forward primer contains a sequence corresponding to a specific region of the DNA polynucleotide, and the reverse primer contains a sequence corresponding to a specific region of the genomic sequence. In addition, the primers used in the PCR assay mixture can comprise at least one forward primers and at least one reverse primer. For example, the KASPar® PCR assay mixture can use two forward primers corresponding to two different alleles and one reverse primer. One of the forward primers contains a sequence corresponding to specific region of the endogenous genomic sequence. The second forward primer contains a sequence corresponding to a specific region of the DNA polynucleotide. The reverse primer contains a sequence corresponding to a specific region of the genomic sequence. Such a KASPar® assay for detection of an amplification reaction is an embodiment of the subject disclosure.

In some embodiments the fluorescent signal or fluorescent dye is selected from the group consisting of a HEX fluorescent dye, a FAM fluorescent dye, a JOE fluorescent dye, a TET fluorescent dye, a Cy 3 fluorescent dye, a Cy 3.5 fluorescent dye, a Cy 5 fluorescent dye, a Cy 5.5 fluorescent dye, a Cy 7 fluorescent dye, and a ROX fluorescent dye.

In other embodiments the amplification reaction is run using suitable second fluorescent DNA dyes that are capable of staining cellular DNA at a concentration range detectable by flow cytometry, and have a fluorescent emission spectrum which is detectable by a real time thermocycler. It should be appreciated by those of ordinary skill in the art that other nucleic acid dyes are known and are continually being identified. Any suitable nucleic acid dye with appropriate excitation and emission spectra can be employed, such as YO-PRO-1®, SYTOX Green®, SYBR Green I®, SYTO11®, SYTO12®, SYTO13®, BOBO®, YOYO®, and TOTO®. In one embodiment, a second fluorescent DNA dye is SYTO13® used at less than 10 µM, less than 4 µM, or less than 2.7 µM.

In further embodiments, Next Generation Sequencing (NGS) can be used for detection. As described by Brautigma et al., 2010, DNA sequence analysis can be used to determine the nucleotide sequence of the isolated and amplified fragment. The amplified fragments can be isolated and sub-cloned into a vector and sequenced using chain-terminator method (also referred to as Sanger sequencing) or Dye-terminator sequencing. In addition, the amplicon can be sequenced with Next Generation Sequencing. NGS technologies do not require the sub-cloning step, and multiple sequencing reads can be completed in a single reaction. Three NGS platforms are commercially available, the Genome Sequencer FLX™ from 454 Life Sciences/Roche, the Illumina Genome Analyser™ from Solexa and Applied Biosystems' SOLiD™ (acronym for: 'Sequencing by Oligo Ligation and Detection'). In addition, there are two single molecule sequencing methods that are currently being developed. These include the true Single Molecule Sequencing (tSMS) from Helicos Bioscience™ and the Single Molecule Real Time™ sequencing (SMRT) from Pacific Biosciences.

The Genome Sequencher FLX™ which is marketed by 454 Life Sciences/Roche is a long read NGS, which uses emulsion PCR and pyrosequencing to generate sequencing reads. DNA fragments of 300-800 bp or libraries containing fragments of 3-20 kb can be used. The reactions can produce over a million reads of about 250 to 400 bases per run for a total yield of 250 to 400 megabases. This technology produces the longest reads but the total sequence output per run is low compared to other NGS technologies.

The Illumina Genome Analyser™ which is marketed by Solexa™ is a short read NGS which uses sequencing by synthesis approach with fluorescent dye-labeled reversible terminator nucleotides and is based on solid-phase bridge PCR. Construction of paired end sequencing libraries containing DNA fragments of up to 10 kb can be used. The reactions produce over 100 million short reads that are 35-76 bases in length. This data can produce from 3-6 gigabases per run.

The Sequencing by Oligo Ligation and Detection (SOLiD) system marketed by Applied Biosystems™ is a short read technology. This NGS technology uses fragmented double stranded DNA that are up to 10 kb in length. The system uses sequencing by ligation of dye-labelled oligonucleotide primers and emulsion PCR to generate one billion short reads that result in a total sequence output of up to 30 gigabases per run.

tSMS of Helicos Bioscience™ and SMRT of Pacific Biosciences™ apply a different approach which uses single DNA molecules for the sequence reactions. The tSMS Helicos™ system produces up to 800 million short reads that result in 21 gigabases per run. These reactions are completed using fluorescent dye-labelled virtual terminator nucleotides that is described as a 'sequencing by synthesis' approach.

The SMRT Next Generation Sequencing system marketed by Pacific Biosciences™ uses a real time sequencing by synthesis. This technology can produce reads of up to 1,000 bp in length as a result of not being limited by reversible terminators. Raw read throughput that is equivalent to one-fold coverage of a diploid human genome can be produced per day using this technology.

In another embodiment, the detection can be completed using blotting assays, including Western blots, Northern blots, and Southern blots. Such blotting assays are commonly used techniques in biological research for the identification and quantification of biological samples. These assays include first separating the sample components in gels by electrophoresis, followed by transfer of the electrophoretically separated components from the gels to transfer membranes that are made of materials such as nitrocellulose, polyvinylidene fluoride (PVDF), or Nylon. Analytes can also be directly spotted on these supports or directed to specific regions on the supports by applying vacuum, capillary action, or pressure, without prior separation. The transfer membranes are then commonly subjected to a post-transfer treatment to enhance the ability of the analytes to be distinguished from each other and detected, either visually or by automated readers.

In a further embodiment the detection can be completed using an ELISA assay, which uses a solid-phase enzyme immunoassay to detect the presence of a substance, usually an antigen, in a liquid sample or wet sample. Antigens from the sample are attached to a surface of a plate. Then, a further specific antibody is applied over the surface so it can bind to the antigen. This antibody is linked to an enzyme, and, in the final step, a substance containing the enzyme's substrate is added. The subsequent reaction produces a detectable signal, most commonly a color change in the substrate.

Transgenic Plants

In an embodiment, a plant, plant tissue, or plant cell comprises a *Zea mays* KN1gene promoter. In one embodiment a plant, plant tissue, or plant cell comprises the *Zea mays* KN1gene promoter of a sequence selected from SEQ ID NO:1 or a sequence that has 80%, 85%, 90%, 95% or 99.5% sequence identity with a sequence selected from SEQ ID NO:1. In an embodiment, a plant, plant tissue, or plant cell comprises a gene expression cassette comprising a sequence selected from SEQ ID NO:1, or a sequence that has 80%, 85%, 90%, 95% or 99.5% sequence identity with a sequence selected from SEQ ID NO:1 that is operably linked to a non-*Zea mays* KN1gene. In an illustrative embodiment, a plant, plant tissue, or plant cell comprises a gene expression cassette comprising a *Zea mays* KN1gene promoter that is operably linked to a transgene, wherein the transgene can be an insecticidal resistance transgene, an herbicide tolerance transgene, a nitrogen use efficiency transgene, a water use efficiency transgene, a nutritional quality transgene, a DNA binding transgene, a selectable marker transgene, or combinations thereof.

In accordance with one embodiment a plant, plant tissue, or plant cell is provided wherein the plant, plant tissue, or plant cell comprises a *Zea mays* KN1gene promoter derived sequence operably linked to a transgene, wherein the *Zea mays* KN1gene promoter derived sequence comprises a sequence SEQ ID NO:1 or a sequence having 80%, 85%, 90%, 95% or 99.5% sequence identity with SEQ ID NO:1. In one embodiment a plant, plant tissue, or plant cell is provided wherein the plant, plant tissue, or plant cell comprises SEQ ID NO: 1, or a sequence that has 80%, 85%, 90%, 95% or 99.5% sequence identity with SEQ ID NO: 1 operably linked to a non-*Zea mays* KN1gene. In one embodiment the plant, plant tissue, or plant cell is a dicotyledonous or monocotyledonous plant or a cell or tissue derived from a dicotyledonous or monocotyledonous plant. In one embodiment the plant is selected from the group consisting of *Zea mays*, wheat, rice, sorghum, oats, rye, bananas, sugar cane, soybean, cotton, sunflower, and canola. In one embodiment the plant is *Zea mays*. In accordance with one embodiment the plant, plant tissue, or plant cell comprises SEQ ID NO: 1 or a sequence having 80%, 85%, 90%, 95% or 99.5% sequence identity with SEQ ID NO:1 operably linked to a non-*Zea mays* KN1 gene. In one embodiment the plant, plant tissue, or plant cell comprises a promoter operably linked to a transgene wherein the promoter consists of SEQ ID NO: for a sequence having 80%, 85%, 90%, 95% or 99.5% sequence identity with SEQ ID NO:1. In accordance with one embodiment the gene construct comprising *Zea mays* KN1gene promoter sequence operably linked to a transgene is incorporated into the genome of the plant, plant tissue, or plant cell.

In an embodiment, a plant, plant tissue, or plant cell according to the methods disclosed herein can be a dicotyledonous plant. The dicotyledonous plant, plant tissue, or plant cell can be, but not limited to alfalfa, rapeseed, canola, Indian mustard, Ethiopian mustard, soybean, sunflower, cotton, beans, broccoli, cabbage, cauliflower, celery, cucumber, eggplant, lettuce; melon, pea, pepper, peanut, potato, pumpkin, radish, spinach, sugarbeet, sunflower, tobacco, tomato, and watermelon.

One of skill in the art will recognize that after the exogenous sequence is stably incorporated in transgenic plants and confirmed to be operable, it can be introduced into other plants by sexual crossing. Any of a number of standard breeding techniques can be used, depending upon the species to be crossed.

The present disclosure also encompasses seeds of the transgenic plants described above, wherein the seed has the transgene or gene construct containing the gene regulatory elements of the subject disclosure. The present disclosure further encompasses the progeny, clones, cell lines or cells of the transgenic plants described above wherein said progeny, clone, cell line or cell has the transgene or gene construct containing the gene regulatory elements of the subject disclosure.

The present disclosure also encompasses the cultivation of transgenic plants described above, wherein the transgenic plant has the transgene or gene construct containing the gene regulatory elements of the subject disclosure. Accordingly, such transgenic plants may be engineered to, inter alia, have one or more desired traits or transgenic events containing the gene regulatory elements of the subject disclosure, by being transformed with nucleic acid molecules according to the invention, and may be cropped or cultivated by any method known to those of skill in the art.

Method of Expressing a Transgene

In an embodiment, a method of expressing at least one transgene in a plant comprises growing a plant comprising a *Zea mays* KN1gene promoter operably linked to at least one transgene or a polylinker sequence. In an embodiment the *Zea mays* KN1gene promoter consists of a sequence selected from SEQ ID NO:1 or a sequence that has 80%, 85%, 90%, 95% or 99.5% sequence identity with a sequence selected from SEQ ID NO:1. In an embodiment, a method of expressing at least one transgene in a plant comprising growing a plant comprising a *Zea mays* KN1gene promoter operably linked to at least one transgene. In an embodiment, a method of expressing at least one transgene in a plant tissue or plant cell comprising culturing a plant tissue or plant cell comprising a *Zea mays* KN1gene promoter operably linked to at least one transgene.

In an embodiment, a method of expressing at least one transgene in a plant comprises growing a plant comprising a gene expression cassette comprising a *Zea mays* KN1gene promoter operably linked to at least one transgene. In one embodiment the *Zea mays* KN1gene promoter consists of a sequence selected from SEQ ID NO:1 or a sequence that has 80%, 85%, 90%, 95% or 99.5% sequence identity with a sequence selected from SEQ ID NO:1. In an embodiment, a method of expressing at least one transgene in a plant comprises growing a plant comprising a gene expression cassette comprising a *Zea mays* KN1gene promoter operably linked to at least one transgene. In an embodiment, a method of expressing at least one transgene in a plant comprises growing a plant comprising a gene expression cassette comprising a *Zea mays* KN1gene promoter operably linked to at least one transgene. In an embodiment, a method of expressing at least one transgene in a plant tissue or plant cell comprises culturing a plant tissue or plant cell comprising a gene expression cassette containing a *Zea mays* KN1gene promoter operably linked to at least one transgene. In an embodiment, a method of expressing at least one transgene in a plant tissue or plant cell comprises culturing a plant tissue or plant cell comprising a gene expression cassette, a *Zea mays* KN1gene promoter operably linked to at least one transgene.

The following examples are provided to illustrate certain particular features and/or embodiments. The examples should not be construed to limit the disclosure to the particular features or embodiments exemplified.

EXAMPLES

Example 1: Novel Design of a Combination of Optimized Regulatory Elements from *Zea mays* KN1 Gene The promoter from a *Zea mays* KN1 gene (SEQ ID NO:1) is a 1,407 bp polynucleotide sequence that was identified from the *Zea mays* genomic DNA (gDNA) sequence. The promoter sequence was identified by BLASTing the Phytozome database (Goodstein D M, Shu S, Howson R, Neupane R, Hayes R D, Fazo J, Mitros T, Dirks W, Hellsten U, Putnam N, Rokhsar D S (2012) *Nucleic Acids Res.* 40: D1178-1186) with a *Zea mays* KN1 gene. The resulting hits were analyzed and a single coding sequence was selected for further analysis. For the identification of a novel promoter region, 1 to 3 kb of nucleotides were retrieved upstream of the translational start site (ATG codon) and additional in silico analyses was performed. These included the identification of polynucleotide sequences from any other surrounding genes as needed, checking for the presence of repetitive sequences that could result in silencing of gene expression, or the presence of 5' UTRs that may contain non-coding exons and introns. Based on these analyses, the *Zea mays* KN1 promoter sequences were synthesized and moved forward for additional usage to drive expression of a transgene. From the assessment of the contiguous chromosomal sequence that spanned millions of base pairs, a 1,407 bp polynucleotide sequence was identified and isolated for use in expression of heterologous coding sequences. This novel polynucleotide sequence was analyzed for use as a regulatory sequence to drive expression of a gene. Accordingly, SEQ ID NO:1 is provided as:

```
ATAAATTTTAACAAGTAAAAAGACTTAACTTGGATAAAAAAATGTTTTCG

TGGGGCGGGTACATGGGGGAACGTGGACGGTCCTCGTGAAACTACGGGGA

TTAAATTTTTCTCCATTTAAATCCCCGCGGGGACTAAATTAGTCTCATAC

CCATCCCCTAATAGGGGAATTTTCCGCGGGGAATTGGGGATCGAGTCCCC

ATTGTCATCTCTACTCTGCGCACGTCTGGATGGTCGCGCCTGGGGCCCGA

ACGGTTCACGATGGCGCAGAGGGTCTTATTTTTCACAGCAGACCTAGATC

TTGCCTCTCGGGAGGGATCCCGTCGGGGAGGAGAGATCCTAGGGTGTGTC

TTGGTGTCAGCAGGCCACCCAAGACGCTTCTAATCGATGTAGAACCGAAG

AAATGCGAAGATTTAAGGTAGAGGAAGGCTAAACTAGAGCTACTCCTAAT

ACAAAATGTAAAAACGATAAGTAAATTTGATCTGATCGAATGTGGGGTT

CAATCGGCCGTAGCCCTTTATATATATAAATGAGAGATCTGAACCCGTTA
```

-continued
CATGTCGTTTACCGAGTTAATCTCGTAGATTTAGCTAACAAATCCCACAA

GAAAATCGAAATCCTAACCGATTCTACACACAAGCGGACCATCCATGCCA

TCACCGCGGATCATCCGGCCTAGCGTCCCCTGCCCAAAAGTGGGCTCAAC

AAGCCTAAATACATATAATTTATACCACGTGCAACACATTTATTCATCCA

TATCACATGTCATGCAAGGCATAAGCATCATGTTAACTTAGTTATACTGA

CATACATTTATGAGTTGAGATGTCCAGGATGTGAGCGCATGAGCCCATTG

TCCATTCAGGACCAAGACAGGCTACTAAGCACTTTCTACATAACTTGTAT

GTGCTAACTATAGCATGCTTATATGGCTCTCTCCAAAGTTCAAAGCTAGC

TCAAATCTTTTGATTTAATAAAACTTAAATTTGTTTGATTTCAGATAAAC

TGATAATTTTTATAATATTTAGAGTGAGTTGAAAACAGAAACTGGCCGCA

AATCCACCTCAAGCCTTTTGATTTGACCTAAAAAAAGAAGCCCCCACAA

ACACCACTCCACACTAGTGCACTGTCTCTCTCCAAAGGCAGCTGCATTGG

CCTCCAGCCTTTTCCCTACTGTGCCGCGCGCCCTCCCTTCTCTCTAATGA

TAGCATAGGGAGAGAAGGCATACTCCGAGGCATCCTTCTCCTTTCCCTCT

CCTTCCCCAAACCCTTTTCCTCTTTCCCTCGCCCAAGAACTTCATCTCA

TCTCCAGGCGCCCTTTTTGCGCTTGCGCAGGAGGAGCTCACGGGACAGT

GGGGCGGAGAGCTCGATCGCTGCTCCACTATTTCAGTGGAGGTCCCTCCC

CAATCCC

Variations of the *Zea mays* KN1 promoter were also designed containing the *Zea mays* alcohol dehydrogenase I intron 6/Maize Streak Virus leader 1 of SEQ ID NO:8 (the *Zea mays* alcohol dehydrogenase I intron 6 is provided individually as SEQ ID NO:7). This variation of the *Zea mays* KN1 promoter is referred to as the *Zea mays* KN1 promoter v2 and disclosed herein as SEQ ID NO:2. Accordingly, SEQ ID NO:2 is provided as:

ATAAATTTTAACAAGTAAAAAGACTTAACTTGGATAAAAAAATGTTT

TCGTGGGCGGGTACATGGGGGAACGTGGACGGTCCTCGTGAAACTA

CGGGGATTAAATTTTTCTCCATTTAAATCCCCGCGGGGACTAAATTA

GTCTCATACCCATCCCCTAATAGGGGAATTTTCCGCGGGGAATTGGG

GATCGAGTCCCCATTGTCATCTCTACTCTGCGCACGTCTGGATGGTC

GCGCCTGGGGCCCGAACGGTTCACGATGGCGCAGAGGGTCTTATTTT

TCACAGCAGACCTAGATCTTGCCTCTCGGGAGGGATCCCGTCGGGGA

GGAGAGATCCTAGGGTGTGTCTTGGTGTCAGCAGGCCACCCAAGACG

CTTCTAATCGATGTAGAACCGAAGAAATGCGAAGATTTAAGGTAGAG

GAAGGCTAAACTAGAGCTACTCCTAATACAAAATGTAAAAACGATAA

GTAAATTTGATCTGATCGAATGTGGGGGTTCAATCGGCCGTAGCCCT

TTATATATAAATGAGAGATCTGAACCCGTTACATGTCGTTTACCG

AGTTAATCTCGTAGATTTAGCTAACAAATCCCACAAGAAAATCGAAA

TCCTAACCGATTCTACACACAAGCGGACCATCCATGCCATCACCGCG

GATCATCCGGCCTAGCGTCCCCTGCCCAAAAGTGGGCTCAACAAGCC

TAAATACATATAATTTATACCACGTGCAACACATTTATTCATCCATA

TCACATGTCATGCAAGGCATAAGCATCATGTTAACTTAGTTATACTG

-continued
ACATACATTTATGAGTTGAGATGTCCAGGATGTGAGCGCATGAGCCC

ATTGTCCATTCAGGACCAAGACAGGCTACTAAGCACTTTCTACATAA

CTTGTATGTGCTAACTATAGCATGCTTATATGGCTCTCTCCAAAGTT

CAAAGCTAGCTCAAATCTTTTGATTTAATAAAACTTAAATTTGTTTG

ATTTCAGATAAACTGATAATTTTTATAATATTTAGAGTGAGTTGAAA

ACAGAAACTGGCCGCAAATCCACCTCAAGCCTTTTGATTTGACCTAA

AAAAAGAAGCCCCCACAAACACCACTCCACACTAGTGCACTGTCTC

TCTCCAAAGGCAGCTGCATTGGCCTCCAGCCTTTTCCCTACTGTGCC

GCGCGCCCTCCCTTCTCTCTAATGATAGCATAGGGAGAGAAGGCATA

CTCCGAGGCATCCTTCTCCTTTCCCTCTCCTTCCCCAAACCCTTTTC

CTCTTTCCCTCGCCCCAAGAACTTCATCTCATCTCCAGGCGCCCTTT

TTGCGCTTGCGCAGGAGGAGCTCACGGGACAGTGGGGCGGAGAGCT

CGATCGCTGCTCCACTATTTCAGTGGAGGTCCCTCCCCAATCCCCTG

AAGGCTCGACAAGGCAGTCCACGGAGGAGCTGATATTTGGTGGACAA

GCTGTGGATAGGAGCAACCCTATCCCTAATATACCAGCACCACCAAG

TCAGGGCAATCCCCAGATCACCCCAGCAGATTCGAAGAAGGTACAGT

ACACACACATGTATATATGTATGATGTATCCCTTCGATCGAAGGCAT

GCCTTGGTATAATCACTGAGTAGTCATTTTATTACTTTGTTTTGACA

AGTCAGTAGTTCATCCATTTGTCCCATTTTTTCAGCTTGGAAGTTTG

GTTGCACTGGCCTTGGTCTAATAACTGAGTAGTCATTTTATTACGTT

GTTTCGACAAGTCAGTAGCTCATCCATCTGTCCCATTTTTTCAGCTA

GGAAGTTTGGTTGCACTGGCCTTGGACTAATAACTGATTAGTCATTT

TATTACATTGTTTCGACAAGTCAGTAGCTCATCCATCTGTCCCATTT

TTCAGCTAGGAAGTTCGGATCTGGGGCCATTTGTTCCAGGCACGGGA

TAAGCATTCAG

Example 2: Vector Construction (pDAB113372 and pDAB1133373)

The pDAB113372 vector was built to incorporate the novel combination of regulatory polynucleotide sequences flanking a transgene. The vector construct pDAB113372 contained a gene expression cassette, in which the GUS-Plus™ transgene (reporter gene from Cambia biosciences) was driven by the *Zea mays* KN1 promoter of SEQ ID NO:1, and flanked by *Zea mays* Peroxidase 5 3' UTR (U.S. Pat. No. 6,699,984). A sequence listing of this gene expression cassette is provided as SEQ ID NO:3. The vector also contained a selectable marker gene expression cassette that contained the aad-1 transgene (U.S. Pat. No. 7,838,733) driven by the *Oryza sativa* Actin1 promoter (U.S. Pat. No. 5,641,876) and was terminated by the *Zea mays* Lipase 3' UTR (U.S. Pat. No. 7,179,902). A sequence listing of this gene expression cassette is provided as SEQ ID NO:4. This construct was built by synthesizing the newly designed promoter from a *Zea mays* KN1 gene (ZmKN1 promoter) and cloning the promoter into a GeneArt Seamless Cloning™ (Life Technologies) entry vector using a third party provider. The resulting entry vector contained the *Zea mays* KN1 gene promoter driving the GUSPlus™ transgene, and was integrated into a destination vector using the Gateway™ cloning system (Life Technologies) and electroporated into *Agrobacterium tumefaciens* strain EHA105 constructed and described by Hood et al, (1993, Transgenic Research 2:208-221). Clones of the resulting binary plasmid, pDAB113372, were obtained and plasmid DNA was isolated and confirmed via restriction enzyme digestions and sequencing. The resulting construct contained a combination of regulatory elements that drive constitutive expression of a transgene.

The pDAB113373 vector was built to incorporate the novel combination of regulatory polynucleotide sequences flanking a transgene. The vector construct pDAB113373 contained a gene expression cassette, in which the GUSPlus™ transgene (reporter gene from Cambia biosciences) was driven by the *Zea mays* KN1 promoter fusion with the *Zea mays* alcohol dehydrogenase I intron 6/Maize Streak Virus leader 1 of SEQ ID NO:2, and flanked by *Zea mays* Peroxidase 5 3' UTR. A sequence listing of this gene expression cassette is provided as SEQ ID NO:6. The vector also contained a selectable marker gene expression cassette that contained the aad-1 transgene driven by the *Oryza sativa* Actin1 promoter and was terminated by the *Zea mays* Lipase 3' UTR. A sequence listing of this gene expression cassette is provided as SEQ ID NO:4. This construct was built by synthesizing the newly designed promoter from a *Zea mays* KN1 gene (ZmKN1 promoter) fused with the *Zea mays* alcohol dehydrogenase I intron 6/Maize Streak Virus leader 1 and cloning the promoter and intron regulatory elements into a GeneArt Seamless Cloning™ (Life Technologies) entry vector using a third party provider. The resulting entry vector contained the *Zea mays* KN1 gene promoter and *Zea mays* alcohol dehydrogenase I intron 6/Maize Streak Virus leader 1 fusion driving the GUSPlus™ transgene, and was integrated into a destination vector using the Gateway™ cloning system (Life Technologies) and electroporated into *Agrobacterium tumefaciens* strain EHA105. Clones of the resulting binary plasmid, pDAB113373, were obtained and plasmid DNA was isolated and confirmed via restriction enzyme digestions and sequencing. The resulting construct contained a combination of regulatory elements that drive constitutive expression of a transgene.

A control construct, pDAB113352, was assembled containing the GUSPlus™ transgene driven by the *Zea mays* Ubiquitin-1 Promoter (Christensen et al., (1992) Plant Molecular Biology 18; 675-689) and *Zea mays* Peroxidase5 3'UTR regulatory elements. The same aad-1 expression cassette as present in pDAB113372. This control construct was transformed into plants using the same reagents and protocols as those for pDAB13372.

Example 3: *Zea mays* Transformation

Inoculation of *Agrobacterium tumefaciens*
The binary expression vectors were transformed into *Agrobacterium tumefaciens* strain EHA105. Bacterial colonies were selected, and binary plasmid DNA was isolated and confirmed via restriction enzyme digestion. The *Agrobacterium* cultures were streaked from glycerol stocks and incubated for growth. On the day of an experiment, the resulting cultures of *Agrobacterium* were used for the transformation of *Zea mays* plants.

Zea mays Transformation
Experimental constructs were transformed into *Zea mays* via *Agrobacterium*-mediated transformation of immature embryos isolated from the inbred line, *Zea mays* c.v. B104. The method used is similar to those published by Ishida et al., (1996) Nature Biotechnol 14:745-750 and Frame et al., (2006) Plant Cell Rep 25: 1024-1034, but with several modifications and improvements to make the method amenable to high-throughput transformation. An example of a method used to produce a number of transgenic events in *Zea mays* is given in U.S. Pat. App. Pub. No. US 2013/0157369 A1, beginning with the embryo infection and co-cultivation steps.

Example 4: Molecular Confirmation of Copy Number at $T_0$

Putative transgenic *Zea mays* plants were sampled at the V2-3 leaf stage for transgene presence using GUSPlus™ and AAD-1 quantitative PCR assays. Total DNA was extracted from leaf punches using MagAttract® DNA extraction kit (Qiagen) as per manufacturer's instruction.

To detect the genes of interest, gene-specific DNA fragments were amplified with TaqMan® primer/probe sets containing a FAM-labeled fluorescent probe for the GUSPlus™ gene and a HEX-labeled fluorescent probe for an endogenous reference gene control.

Next, the PCR reactions were carried out in a final volume of 10 µl reaction containing 5 µl of Roche LightCycler® 480 Probes Master Mix (Roche Applied Sciences, Indianapolis, Ind.); 0.4 µl each of the primers from 10 µM stocks to a final concentration of 400 nM; 0.4 µl each of the probes from 5 µM stocks to a final concentration of 200 nM, 0.1 µl of 10% polyvinylpyrrolidone (PVP) to final concentration of 0.1%; 2 µl of 10 ng/µl genomic DNA and 0.5 µl water. The DNA was amplified in a Roche LightCycler® 480 System under the following conditions: 1 cycle of 95° C. for 10 min; 40 cycles of the following 3-steps: 95° C. for 10 seconds; 58° C. for 35 seconds and 72° C. for 1 second, and a final cycle of 4° C. for 10 seconds. Cry34Ab1 copy number was determined by comparison of Target (gene of interest)/Reference (Invertase gene) values for unknown samples (output by the LightCycler® 480) to Target/Reference values of GUSPlus™ copy number controls.

The detection of the AAD-1 gene was carried out as described above for the GUSPlus™ gene using an endogenous reference gene.

$T_0$ plants were selfed and crossed to *Zea mays* c.v. B104 non-transgenic transformation lines to obtain $T_1$ seed. Five-six transgenic lines or events of each of the test regulatory element constructs were advanced for $T_1$ reporter protein studies. Accordingly, 30-40 $T_1$ seed of each of the events were sown; seedlings were sprayed with SureII® at the V2-3 stage of development to kill non-transgenic segregants.

Example 5: Molecular Confirmation of GUS Enzyme Activity

Germination
Next, the transgenic plants were grown in greenhouse environmental conditions were set for 29° C. day temperature and 26° C. night temperature with 14 hour lighting day. Greenhouse lighting is a mixture of high pressure sodium vapor and metal halide lamps. T1 seed from events defined in Table 2 were sown 3.5 cm deep, one kernel per plug into a QPlug 60 (International Horticultural Technologies). The seed was then covered with fine vermiculite, and QPlugs placed in greenhouse.

Stage Sample Collection
Root and leaf sample collection was completed following standard methodology. A 1-cm section of root tissue was collected per sample. Leaf tissue samples were collected for transcript analysis at the V03, V06 and V10 stages. Samples were collected and preserved for RNA extractions. Each sample was placed into a labeled 1.4 mL matrix tube (Thermo Scientific) and capped with a Micronic pierceable TPE Cap™ (Nova Biostorage Plus). Sample tubes were flash frozen for 3-5 seconds in liquid nitrogen and then transferred to a 96-well rack on dry ice. Samples were stored at approximately −80° C.

Transcript Abundance Analysis

Total RNA was isolated and purified from frozen tissue samples in a 96-well plate format using the MagMAX™ 96 Total RNA Isolation Kit (Life Technologies) with the Mag-MAX™ Express-96 Deep Well Magnetic Particle Processor instrument. Sample processing steps were implemented. cDNA synthesis, quantitative real-time PCR assays, and data analysis were performed. Raw data in the form of cycle threshold (Cq) for the target PhiYFP assay was normalized to the internal reference genes. Target to reference ratios were calculated according to the formula $2^{-(C_q TARGET - C_q REF)}$. The geometric mean of two reference gene normalized ratios was calculated to increase accuracy (Vandesompele J, De Preter K, Pattyn F, Poppe B, Van Roy N, De Paepe A, Speleman F (2002) *Genome biology* 3: research0034). Samples from each tissue used a specific combination of reference gene pairs optimized for that particular tissue.

GUS Activity Staining and Microscopy of Immature Ears

Immature ears were collected from the greenhouse, dissected out of the husk leaves, and cut into approximately 5 mm thick cross sections. Sections of ear were fixed in ice cold 75% acetone, vacuumed briefly, and allowed to fix overnight at 4° C. Samples were exchanged to 10 mM PBS, vacuumed again, and put on a slow rotator for 4 hours. Samples were exchanged to fresh PBS, and the stained in X-GlcA staining solution (Sigma-Aldrich) overnight at RT on a rotator. Samples were then rinsed in fresh PBS, and dehydrated in graded ethanol (25, 50, 75, 100%). Images were taken of the stained ear section using a Leica M205FA Stereomicroscope™ Samples were then cleared in xylene (25, 50, 75, 100%), and infiltrated with paraffin. Sections were cut at 7 μm thickness, de-waxed in xylene, and mounted unstained in Polymount-Xylene™ (Polysciences). Images were taken of sections using a Leica DM5000 Microscope™

Example 6: Expression Profiles of Genes Operably Linked to the Zea mays KN1 Regulatory Element in Crop Plants The *Zea mays* KN1 promoter regulatory element of SEQ ID NO:1, as provided in pDAB113372, resulted in reproductive meristematic tissue expression of the GUSPlus™ gene in *Zea mays* transgenic plant events. Upon analysis of the data generated above the robust expression of the GUSPlus™ gene in various tissue types and at different development stages was determined. For example, the *Zea mays* KN1 promoter regulatory element drove expression in reproductive meristematic tissues such as developing *Zea mays* cob and silk tissues. It was noted that low levels of the GUSPlus™ gene was expressed in immature male florets. Furthermore, the expression of the expression of the GUS-Plus™ gene in leaves and roots of *Zea mays* plants was undetectable. Comparatively, there was constitutive expression of the GUSPlus™ gene observed or detected in plant events transformed with the control construct, pDAB113352. This construct, pDAB113352, contain the GUSPlus™ transgene under the expression of the *Zea mays* Ubiquitin 1 promoter. All constructs expressed the aad-1 gene in the tissues that were assayed.

As such, novel a *Zea mays* KN1 gene regulatory element (SEQ ID NO:1) was identified and characterized. Disclosed for the first time are novel promoter regulatory elements for use in gene expression constructs.

Example 7: *Agrobacterium*-Mediated Transformation of Genes Operably Linked to the Zea mays KN1 Promoter Soybean may be transformed with genes operably linked to the *Zea mays* KN1 promoter by utilizing the same techniques previously described in Example #11 or Example #13 of patent application WO 2007/053482.

Cotton may be transformed with genes operably linked to the *Zea mays* KN1 promoter by utilizing the same techniques previously described in Examples #14 of U.S. Pat. No. 7,838,733 or Example #12 of patent application WO 2007/053482 (Wright et al.).

Canola may be transformed with genes operably linked to the *Zea mays* KN1 promoter by utilizing the same techniques previously described in Example #26 of U.S. Pat. No. 7,838,733 or Example #22 of patent application WO 2007/053482 (Wright et al.).

Wheat may be transformed with genes operably linked to the *Zea mays* KN1 promoter by utilizing the same techniques previously described in Example #23 of patent application WO 2013/116700A1 (Lira et al.).

Rice may be transformed with genes operably linked to the *Zea mays* KN1 promoter by utilizing the same techniques previously described in Example #19 of patent application WO 2013/116700A1 (Lira et al.).

Example 8: *Agrobacterium*-mediated Transformation of Genes Operably Linked to the Zea mays KN1 Regulatory Element In light of the subject disclosure, additional crops can be transformed according to embodiments of the subject disclosure using techniques that are known in the art. For *Agrobacterium*-mediated transformation of rye, see, e.g., Popelka J C, Xu J, Altpeter F., "Generation of rye with low transgene copy number after biolistic gene transfer and production of (*Secale cereale* L.) plants instantly marker-free transgenic rye," Transgenic Res. 2003 October; 12(5):587-96.). For *Agrobacterium*-mediated transformation of sorghum, see, e.g., Zhao et al., "*Agrobacterium*-mediated sorghum transformation," Plant Mol Biol. 2000 December; 44(6):789-98. For *Agrobacterium*-mediated transformation of barley, see, e.g., Tingay et al., "*Agrobacterium tumefaciens*-mediated barley transformation," The Plant Journal, (1997) 11: 1369-1376. For *Agrobacterium*-mediated transformation of wheat, see, e.g., Cheng et al., "Genetic Transformation of Wheat Mediated by *Agrobacterium tumefaciens*," Plant Physiol. 1997 November; 115(3):971-980. For *Agrobacterium*-mediated transformation of rice, see, e.g., Hiei et al., "Transformation of rice mediated by *Agrobacterium tumefaciens*," Plant Mol. Biol. 1997 September; 35(1-2):205-18.

The Latin names for these and other plants are given below. It should be clear that other (non-*Agrobacterium*) transformation techniques can be used to transform genes operably linked to the *Zea mays* KN1 promoter, for example, into these and other plants. Examples include, but are not limited to; Maize (*Zea mays*), Wheat (*Triticum* spp.), Rice (*Oryza* spp. and *Zizania* spp.), Barley (*Hordeum* spp.), Cotton (*Abroma augusta* and *Gossypium* spp.), Soybean (*Glycine max*), Sugar and table beets (*Beta* spp.), Sugar cane (*Arenga pinnata*), Tomato (*Lycopersicon esculentum* and other spp., *Physalis ixocarpa, Solanum incanum* and other spp., and *Cyphomandra betacea*), Potato (*Solanum tuberosum*), Sweet potato (*Ipomoea batatas*), Rye (*Secale* spp.), Peppers (*Capsicum annuum, chinense*, and *frutescens*), Lettuce (*Lactuca sativa, perennis*, and *pulchella*), Cabbage (*Brassica* spp.), Celery (*Apium graveolens*), Eggplant (*Solanum melongena*), Peanut (*Arachis hypogea*), Sorghum (*Sorghum* spp.), Alfalfa (*Medicago sativa*), Carrot (*Daucus carota*), Beans (*Phaseolus* spp. and other genera), Oats (*Avena sativa* and *strigosa*), Peas (*Pisum, Vigna*, and *Tetragonolobus* spp.), Sunflower (*Helianthus annuus*), Squash (*Cucurbita* spp.), Cucumber (*Cucumis sativa*), Tobacco (*Nicotiana* spp.), Arabidopsis (*Arabidopsis thaliana*), Turfgrass (*Lolium, Agrostis, Poa, Cynodon*, and other genera), Clover (*Trifolium*), Vetch (*Vicia*). Transformation of such plants, with genes operably linked to the 3' UTR of *Arabidopsis thaliana* Ubiquitin 10, for example, is contemplated in embodiments of the subject disclosure.

Use of the *Zea mays* KN1 promoter to drive operably linked genes can be deployed in many deciduous and evergreen timber species. Such applications are also within the scope of embodiments of this disclosure. These species include, but are not limited to; alder (*Alnus* spp.), ash (*Fraxinus* spp.), aspen and poplar species (*Populus* spp.), beech (*Fagus* spp.), birch (*Betula* spp.), cherry (*Prunus* spp.), eucalyptus (*Eucalyptus* spp.), hickory (*Carya* spp.), maple (*Acer* spp.), oak (*Quercus* spp.), and pine (*Pinus* spp.).

Use of *Zea mays* KN1 promoter to drive operably linked genes can be deployed in ornamental and fruit-bearing species. Such applications are also within the scope of embodiments of this disclosure. Examples include, but are not limited to; rose (*Rosa* spp.), burning bush (*Euonymus* spp.), petunia (*Petunia* spp.), begonia (*Begonia* spp.), rhododendron (*Rhododendron* spp.), crabapple or apple (*Malus* spp.), pear (*Pyrus* spp.), peach (*Prunus* spp.), and marigolds (*Tagetes* spp.).

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A nucleic acid vector comprising a promoter operably linked to a heterologous polynucleotide sequence of:
   a) a polylinker sequence;
   b) a non-*Zea mays* KNI gene; or
   c) a combination of a) and b), wherein said promoter comprises a polynucleotide sequence that has at least 99% sequence identity with SEQ ID NO:1.

2. The nucleic acid vector of claim 1, wherein said promoter is 1,407 bp in length.

3. The nucleic acid vector of claim 1, wherein said promoter consists of a polynucleotide sequence that has at least 99% sequence identity with SEQ ID NO:1.

4. The nucleic acid vector of any one of claims 1-3, further comprising a sequence encoding a selectable marker.

5. The nucleic acid vector of claim 1, wherein said promoter is operably linked to a transgene.

6. The nucleic acid vector of claim 5, wherein the transgene encodes a selectable marker or a gene product conferring insecticidal resistance, herbicide tolerance, nitrogen use efficiency, water use efficiency, expression of an RNAi, or nutritional quality.

7. The nucleic acid vector of any of claim 1-3, or 5, further comprising a 3' untranslated polynucleotide sequence.

8. The nucleic acid vector of any of claim 1-3, or 5, further comprising an operably linked 5' untranslated polynucleotide sequence.

9. The nucleic acid vector of any of claim 1-3, or 5, further comprising an intron sequence.

10. The nucleic acid vector of claim 1, wherein said promoter has reproductive meristematic tissue specific expression.

11. A transgenic plant comprising a polynucleotide sequence that has at least 99% sequence identity with SEQ ID NO:1 operably linked to a transgene.

12. The transgenic plant of claim 11, wherein said plant is selected from the group consisting of *Zea mays*, wheat, rice, sorghum, oats, rye, bananas, sugar cane, soybean, cotton, *Arabidopsis*, tobacco, sunflower, and canola.

13. The transgenic plant of claim 12, wherein said plant is *Zea mays*.

14. The transgenic plant of claim 11, further comprising a 3' untranslated sequence.

15. The transgenic plant of claim 11, wherein said transgene is expressed specifically in reproductive meristematic.

16. The transgenic plant of claim 11, wherein said polynucleotide sequence is 1,407 bp in length.

17. A method for producing a transgenic plant cell, the method comprising the steps of:
   a) transforming a plant cell with a gene expression cassette comprising a *Zea mays* KN1 promoter, wherein said *Zea mays* KN1 promoter comprises a polynucleotide sequence that has at least 99% sequence identity with SEQ ID NO:1, operably linked to at least one polynucleotide sequence of interest;
   b) isolating the transformed plant cell comprising the gene expression cassette; and,
   c) producing a transgenic plant cell comprising the *Zea mays* KN1 promoter operably linked to at least one polynucleotide sequence of interest.

18. The method of claim 17, wherein transforming a plant cell is performed with a plant transformation method.

19. The method of claim 18, wherein the plant transformation method is selected from the group consisting of an *Agrobacterium*-mediated transformation method, a biolistics transformation method, a silicon carbide transformation method, a protoplast transformation method, and a liposome transformation method.

20. The method of claim 17, wherein the polynucleotide sequence is expressed specifically in reproductive meristematic.

21. The method of claim 17, wherein the *Zea mays* KN1 promoter operably linked to at least one polynucleotide sequence of interest is stably integrated into the genome of the transgenic plant cell.

22. The method of claim 17, the method further comprising the steps of:
   d) regenerating the transgenic plant cell into a transgenic plant; and,
   e) obtaining the transgenic plant, wherein the transgenic plant comprises the gene expression cassette comprising the *Zea mays* KN1 promoter operably linked to at least one polynucleotide sequence of interest.

23. The method of claim 17, wherein the transgenic plant cell is a monocotyledonous transgenic plant cell or a dicotyledonous transgenic plant cell.

24. The method of claim 23, wherein the dicotyledonous transgenic plant cell is selected from the group consisting of an *Arabidopsis* plant cell, a tobacco plant cell, a soybean plant cell, a canola plant cell, and a cotton plant cell.

25. The method of claim 23, wherein the monocotyledonous transgenic plant cell is selected from the group consisting of a *Zea mays* plant cell, a rice plant cell, and a wheat plant cell.

26. The *Zea mays* KN1 promoter of claim 17, the *Zea mays* KN1 promoter comprising the polynucleotide of SEQ ID NO:1.

\* \* \* \* \*